(12) United States Patent  
Niederberger et al.

(10) Patent No.: US 9,113,969 B2  
(45) Date of Patent: Aug. 25, 2015

(54) BONE FIXATION SYSTEMS AND METHODS OF USE

(71) Applicant: DePuy Synthes Products, Inc., Raynham, MA (US)

(72) Inventors: Alfred Niederberger, Zuchwil (CH); Johann Fierlbeck, Saltzburg (AT); Alexander Hatt, Zuchwil (CH); Guido Hertig, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/256,588

(22) Filed: Apr. 18, 2014

(65) Prior Publication Data

US 2014/0214090 A1    Jul. 31, 2014

Related U.S. Application Data

(63) Continuation of application No. 13/095,162, filed on Apr. 27, 2011, now Pat. No. 8,740,915.

(60) Provisional application No. 61/328,347, filed on Apr. 27, 2010, provisional application No. 61/328,381, filed on Apr. 27, 2010.

(51) Int. Cl.
  *A61B 17/88*    (2006.01)
  *A61B 17/66*    (2006.01)
  (Continued)

(52) U.S. Cl.
  CPC ......... *A61B 17/8019* (2013.01); *A61B 17/8057* (2013.01); *A61B 17/848* (2013.01); *A61B 17/86* (2013.01); *A61B 17/8872* (2013.01); *A61B 2017/90* (2013.01); *Y10S 606/915* (2013.01)

(58) Field of Classification Search
  USPC ................... 606/99, 105, 205, 207, 281, 282
  See application file for complete search history.

(56) References Cited

U.S. PATENT DOCUMENTS

| | | |
|---|---|---|
| 1,649,423 A | 11/1927 | Stieglitz |
| 2,644,455 A | 7/1953 | Benoit |

(Continued)

FOREIGN PATENT DOCUMENTS

| | | |
|---|---|---|
| CN | 201227320 Y | 4/2009 |
| DE | 7315277 U9 | 8/1973 |

(Continued)

OTHER PUBLICATIONS

U.S. Appl. No. 61/328,278, filed Apr. 27, 2010, Kolb et al.

(Continued)

*Primary Examiner* — David Bates
(74) *Attorney, Agent, or Firm* — Baker & Hostetler LLP

(57) ABSTRACT

A bone fixation system that may be configured to move at least one of a first bone segment and a second bone segment relative to the other, is disclosed. The system may include a first lever and a second lever pivotally coupled to the first lever. The first lever may include a first handle, a first jaw extending from the first handle, and an aperture extending through the first jaw. The aperture may be configured to receive a fixation element to thereby fixedly couple the first lever to a bone plate. The second lever may include a second handle, a second jaw extending from the second handle, and an aperture extending through the second jaw. The aperture may be configured to receive a temporary fixation element to operatively couple the second lever to the second bone segment.

14 Claims, 15 Drawing Sheets

(51) Int. Cl.
*A61B 17/58* (2006.01)
*A61B 17/60* (2006.01)
*A61F 2/00* (2006.01)
*A61B 17/00* (2006.01)
*A61B 17/80* (2006.01)
A61B 17/84 (2006.01)
A61B 17/86 (2006.01)
A61B 17/90 (2006.01)

(56) References Cited

U.S. PATENT DOCUMENTS

| | | | |
|---|---|---|---|
| 2,977,150 A | 3/1961 | Thomas | |
| 3,209,753 A | 10/1965 | Hawkins et al. | |
| 3,647,186 A | 3/1972 | Hartman | |
| 4,024,870 A | 5/1977 | Sandel | |
| 4,119,092 A * | 10/1978 | Gil | 606/96 |
| 4,192,313 A | 3/1980 | Ogami | |
| 4,844,068 A | 7/1989 | Arata et al. | |
| 4,887,612 A | 12/1989 | Esser et al. | |
| 4,898,161 A * | 2/1990 | Grundei | 606/105 |
| 5,147,369 A | 9/1992 | Wagner | |
| 5,167,662 A * | 12/1992 | Hayes et al. | 606/916 |
| 5,281,223 A | 1/1994 | Ray | |
| 5,391,181 A | 2/1995 | Johnson et al. | |
| 5,562,447 A | 10/1996 | Moy et al. | |
| 5,578,032 A * | 11/1996 | Lalonde | 606/54 |
| 5,616,143 A * | 4/1997 | Schlapfer et al. | 606/86 A |
| 5,624,454 A | 4/1997 | Palti et al. | |
| 5,676,666 A * | 10/1997 | Oxland et al. | 606/86 B |
| 5,693,069 A | 12/1997 | Shallman | |
| 5,697,933 A | 12/1997 | Gundlapalli et al. | |
| 5,746,757 A | 5/1998 | McGuire | |
| 5,891,161 A | 4/1999 | Graser | |
| 6,036,692 A | 3/2000 | Burel et al. | |
| 6,206,881 B1 | 3/2001 | Frigg et al. | |
| 6,306,136 B1 | 10/2001 | Baccelli | |
| 6,332,887 B1 * | 12/2001 | Knox | 606/87 |
| 6,551,316 B1 | 4/2003 | Rinner et al. | |
| 6,648,891 B2 * | 11/2003 | Kim | 606/86 B |
| 6,660,006 B2 | 12/2003 | Markworth et al. | |
| 6,716,218 B2 | 4/2004 | Holmes et al. | |
| 6,746,449 B2 | 6/2004 | Jones et al. | |
| 7,011,658 B2 * | 3/2006 | Young | 606/258 |
| 7,044,947 B2 | 5/2006 | de la Torre et al. | |
| 7,210,378 B1 | 5/2007 | Bibi | |
| 7,326,218 B2 | 2/2008 | Sterett et al. | |
| 7,341,594 B2 | 3/2008 | Shluzas et al. | |
| 7,540,874 B2 * | 6/2009 | Trumble et al. | 606/79 |
| 7,625,376 B2 | 12/2009 | Brumfield et al. | |
| 7,641,176 B2 | 1/2010 | Clark et al. | |
| 7,713,274 B2 | 5/2010 | Shluzas et al. | |
| 7,744,598 B2 | 6/2010 | Brumfield et al. | |
| 7,815,650 B2 | 10/2010 | Shluzas et al. | |
| 7,988,700 B2 | 8/2011 | Shluzas et al. | |
| 8,152,834 B2 | 4/2012 | McGarity et al. | |
| 8,647,120 B2 | 2/2014 | Marteney et al. | |
| 8,740,915 B2 | 6/2014 | Niederberger et al. | |
| 8,834,485 B2 * | 9/2014 | Kave | 606/102 |
| 2005/0004590 A1 | 1/2005 | Waters et al. | |
| 2005/0191598 A1 | 9/2005 | Anderson | |
| 2006/0004380 A1 * | 1/2006 | DiDomenico et al. | 606/105 |
| 2007/0173836 A1 | 7/2007 | Prien | |
| 2007/0203492 A1 * | 8/2007 | Needham et al. | 606/61 |
| 2007/0244516 A1 | 10/2007 | Chiu et al. | |
| 2007/0270850 A1 * | 11/2007 | Geissler | 606/69 |
| 2008/0140130 A1 | 6/2008 | Chan et al. | |
| 2008/0234689 A1 * | 9/2008 | Melkent et al. | 606/99 |
| 2008/0287995 A1 | 11/2008 | Gauthier | |
| 2009/0182345 A1 | 7/2009 | Medoff et al. | |
| 2009/0248084 A1 | 10/2009 | Hinterman | |
| 2009/0259262 A1 | 10/2009 | Nayet | |
| 2010/0016900 A1 * | 1/2010 | Terres et al. | 606/280 |
| 2010/0168799 A1 * | 7/2010 | Schumer | 606/286 |
| 2010/0280560 A1 | 11/2010 | Brumfield et al. | |
| 2011/0098757 A1 * | 4/2011 | Schelling | 606/324 |
| 2011/0154958 A1 | 6/2011 | Wang | |
| 2011/0224734 A1 | 9/2011 | Schelling | |
| 2011/0264149 A1 * | 10/2011 | Pappalardo et al. | 606/286 |
| 2012/0197304 A1 * | 8/2012 | Medoff et al. | 606/286 |

FOREIGN PATENT DOCUMENTS

| | | |
|---|---|---|
| DE | 20 2006 008031 U1 | 10/2007 |
| EP | 1319372 A1 | 6/2003 |
| EP | 1319372 B1 | 6/2003 |
| EP | 1923009 A2 | 5/2008 |
| EP | 1923009 A3 | 6/2009 |
| JP | 2007-190390 | 8/2007 |
| JP | 2011-515172 | 5/2011 |
| WO | WO 96/24295 A1 | 8/1996 |
| WO | WO 03/030395 A2 | 4/2003 |
| WO | WO 2006/047581 A2 | 5/2006 |
| WO | WO 2006/074792 | 7/2006 |
| WO | WO 2007/127994 | 11/2007 |
| WO | WO 2009/118461 | 10/2009 |
| WO | WO 2010/011477 | 1/2010 |
| WO | WO 2011/053520 | 5/2011 |
| WO | WO 2011/137163 | 11/2011 |
| WO | WO 2011/139740 | 11/2011 |

OTHER PUBLICATIONS

U.S. Appl. No. 61/372,212, filed Aug. 10, 2010, Kolb et al.
U.S. Appl. No. 61/328,347, filed Apr. 27, 2010, Niederberger et al.
U.S. Appl. No. 61/328,381, filed Apr. 27, 2010, Niederberger et al.

* cited by examiner

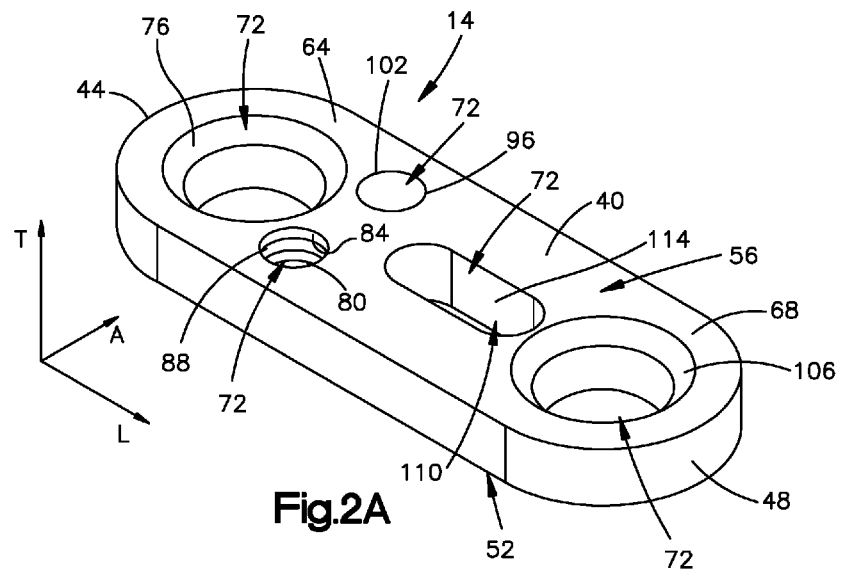
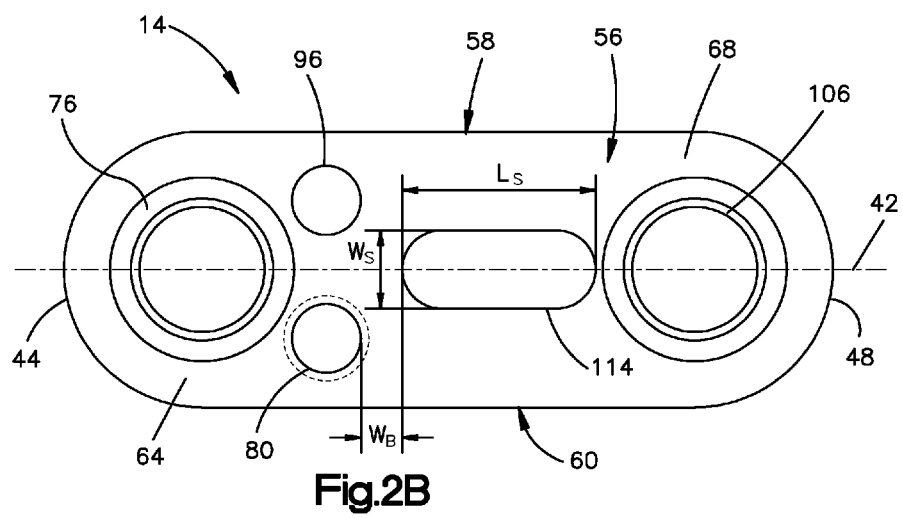

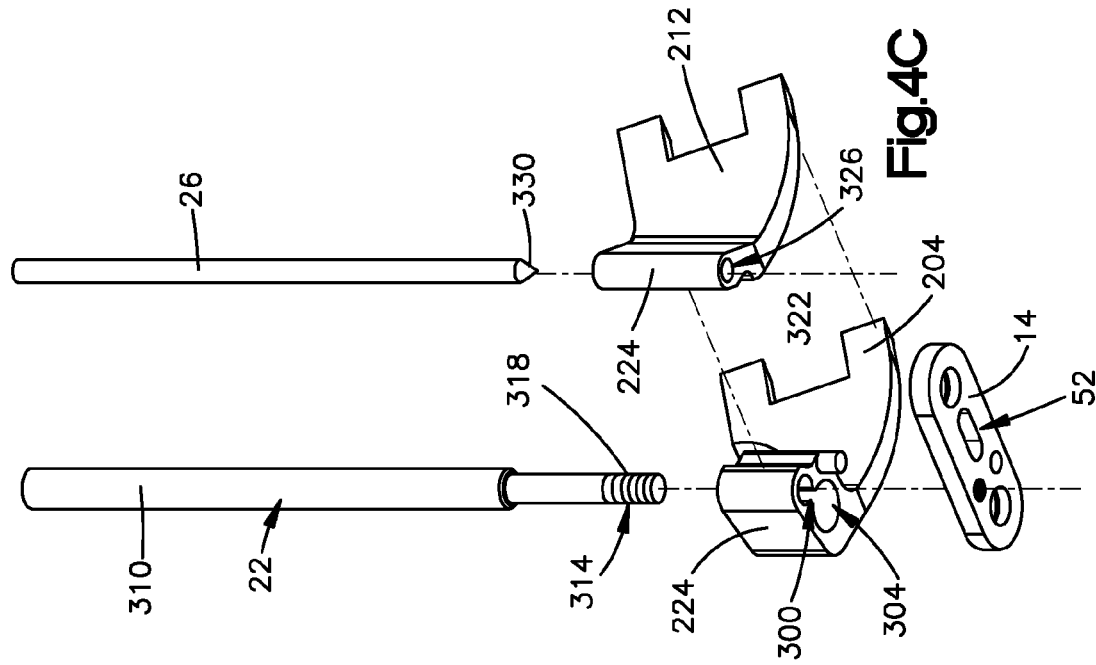
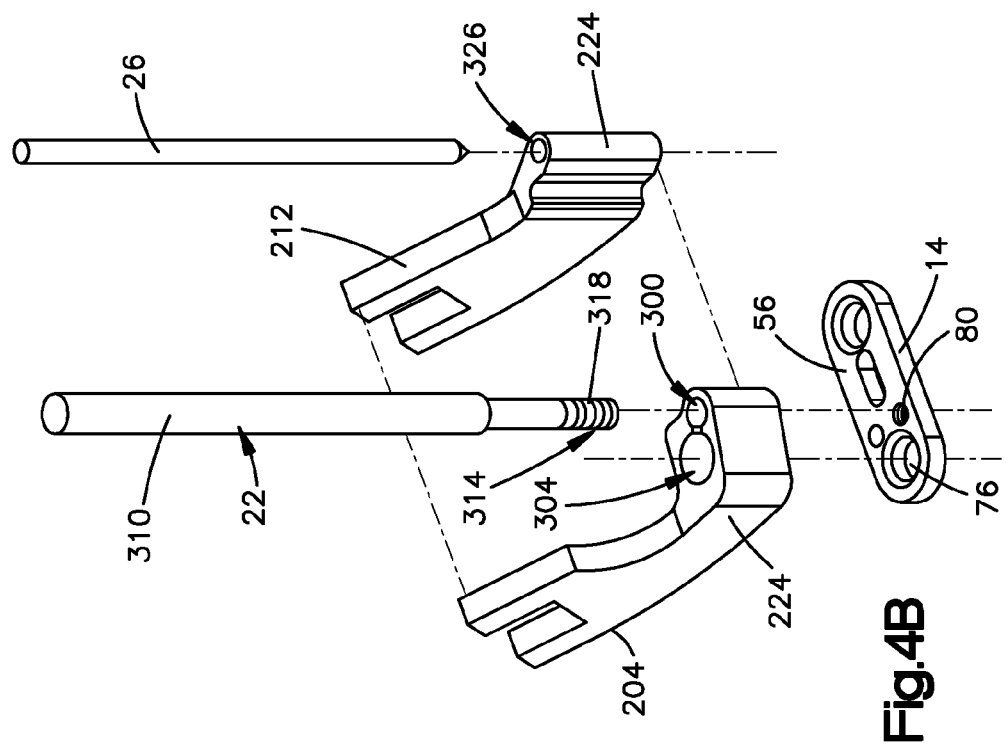

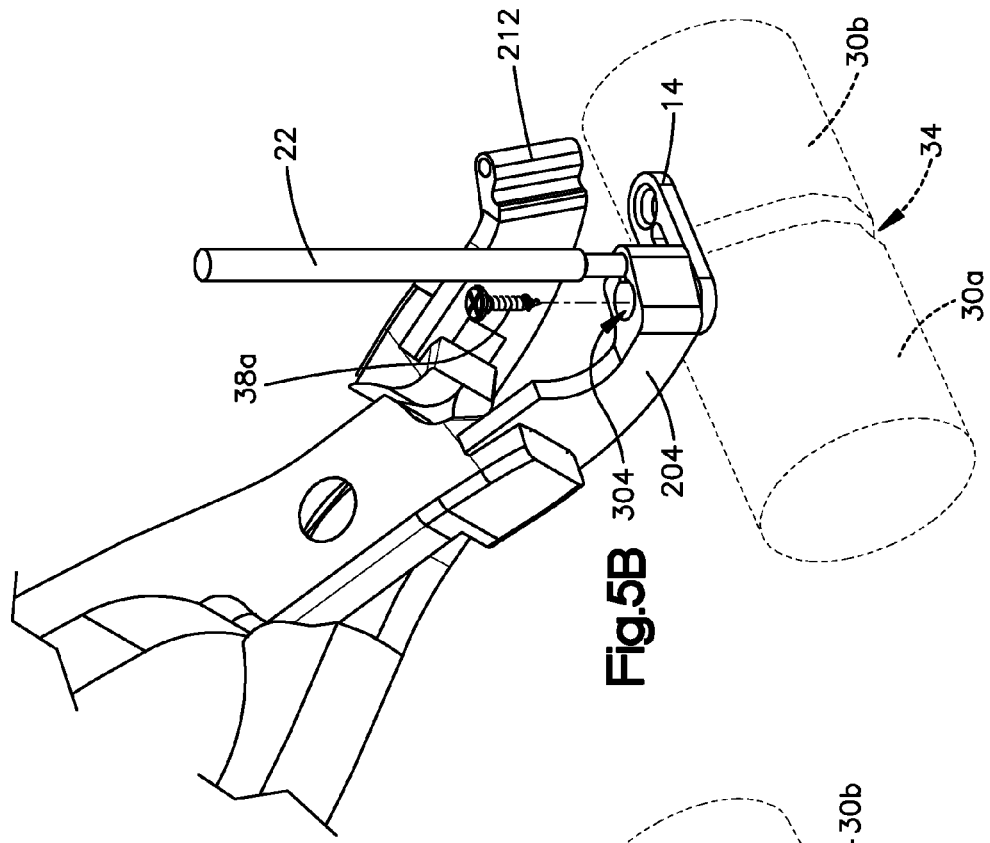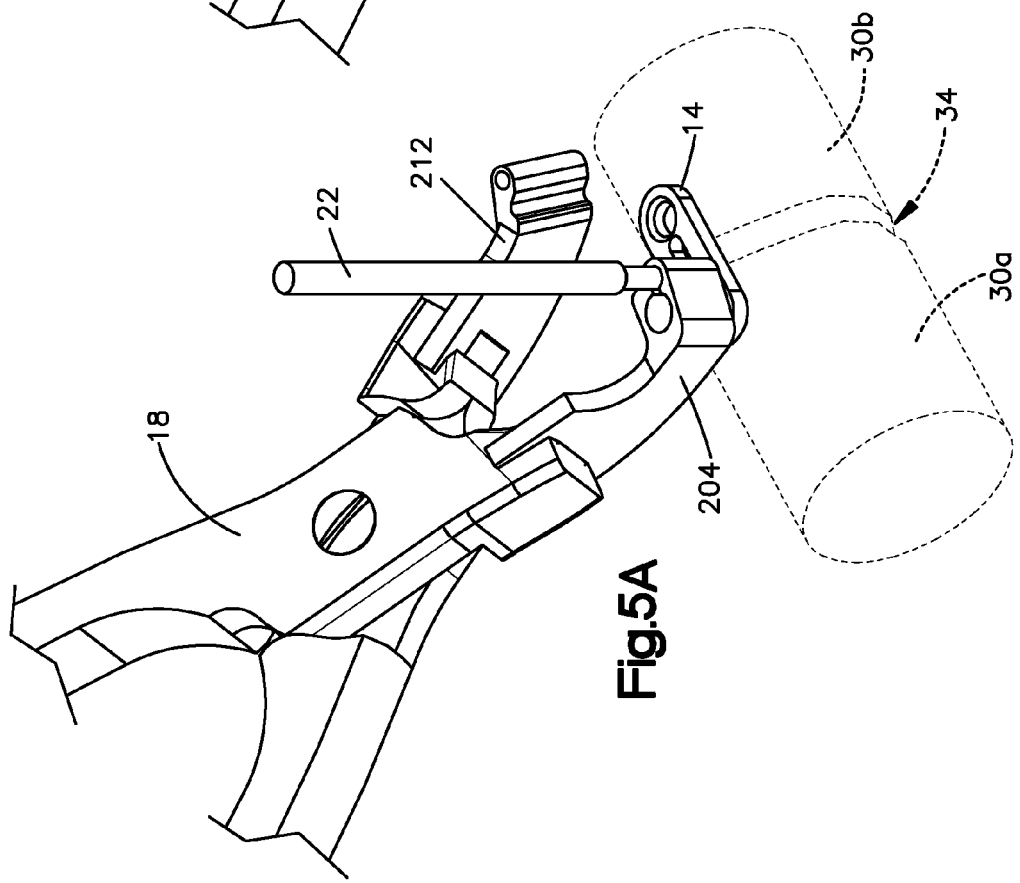

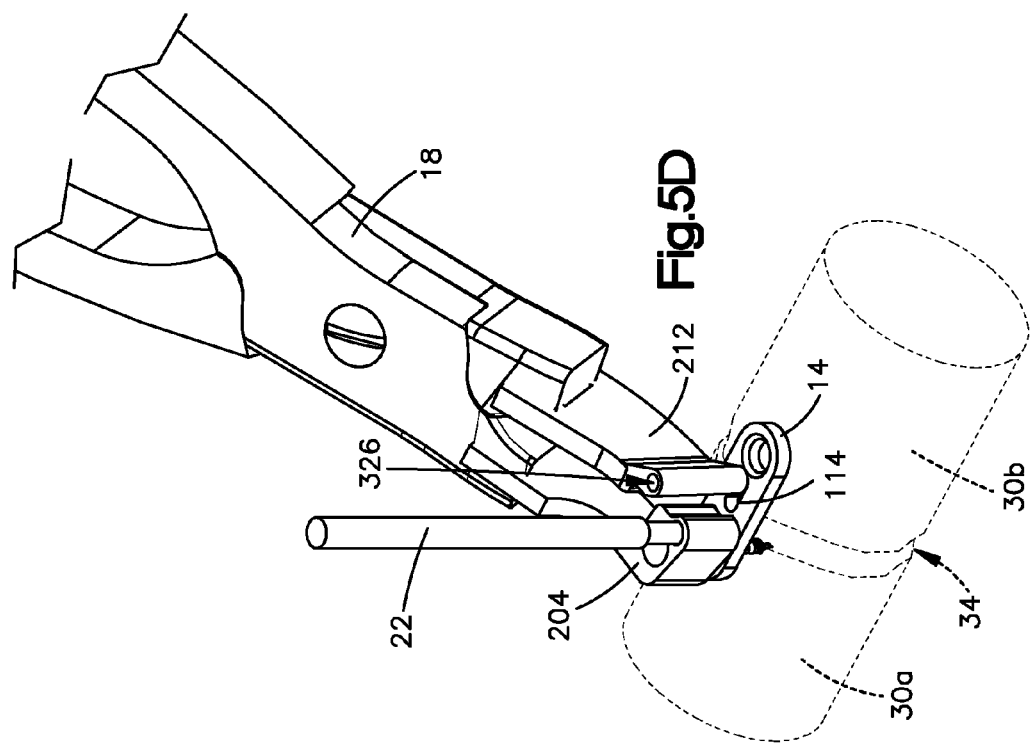
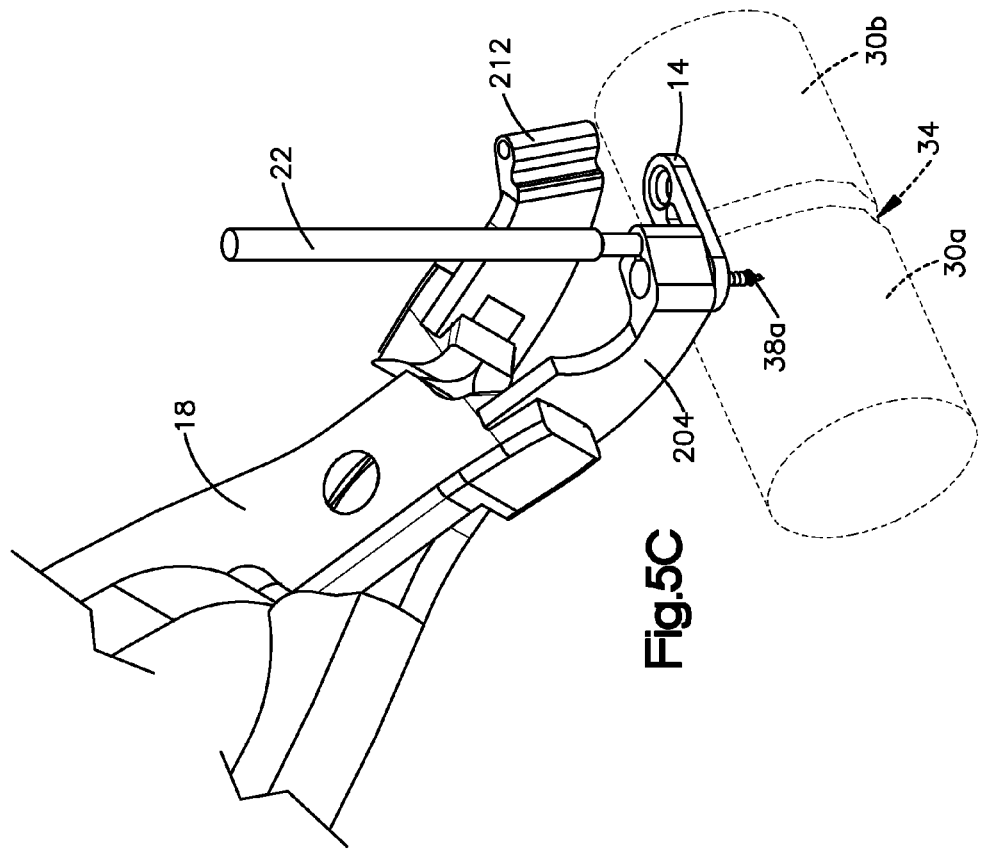

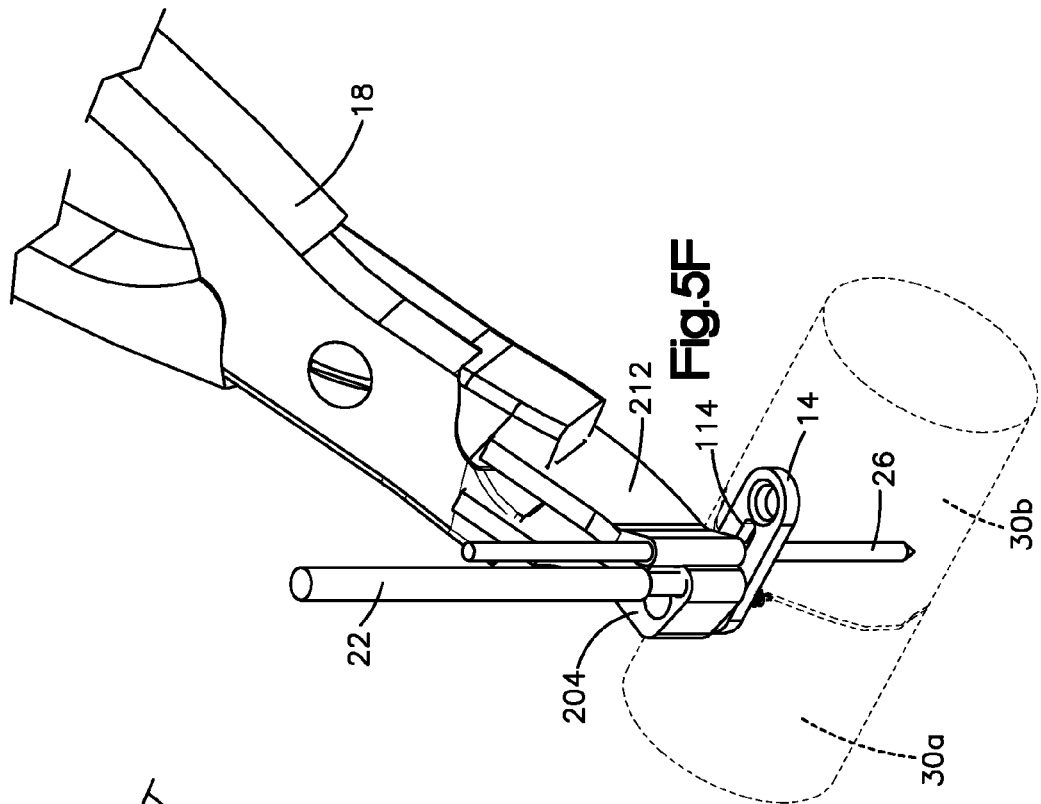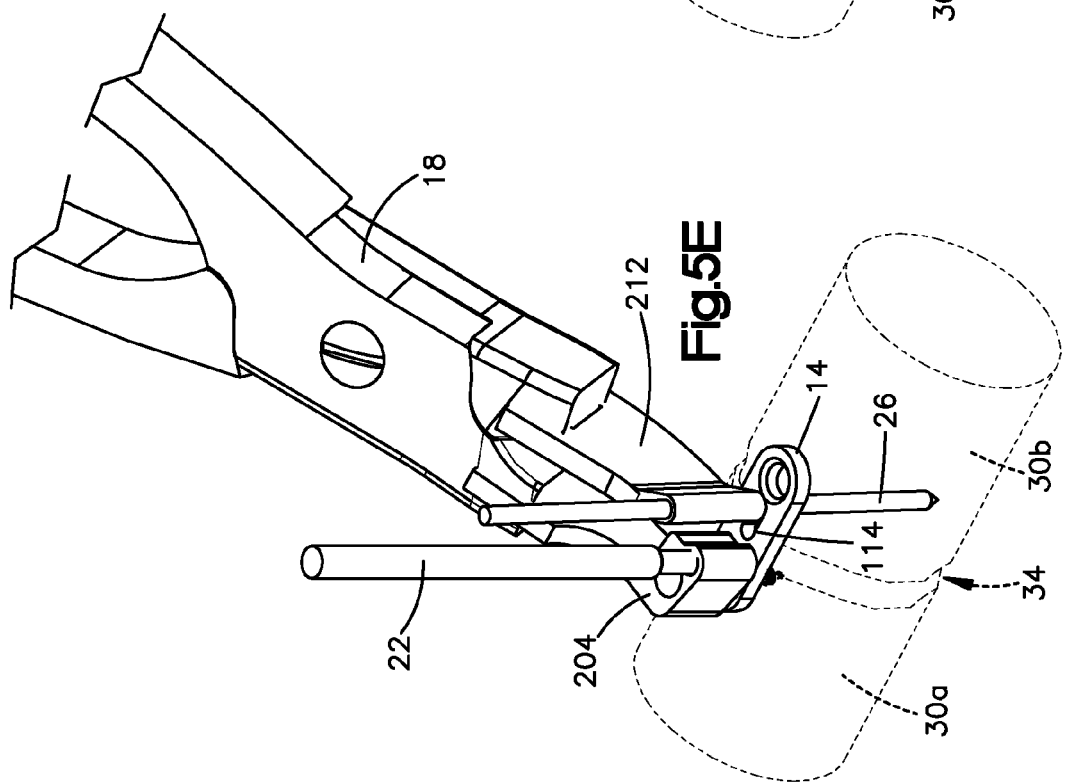

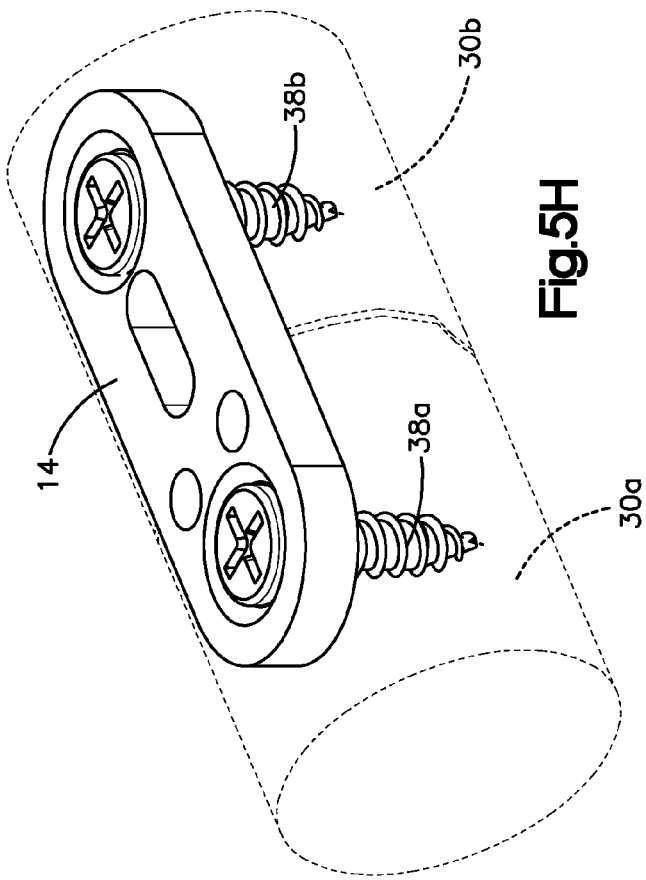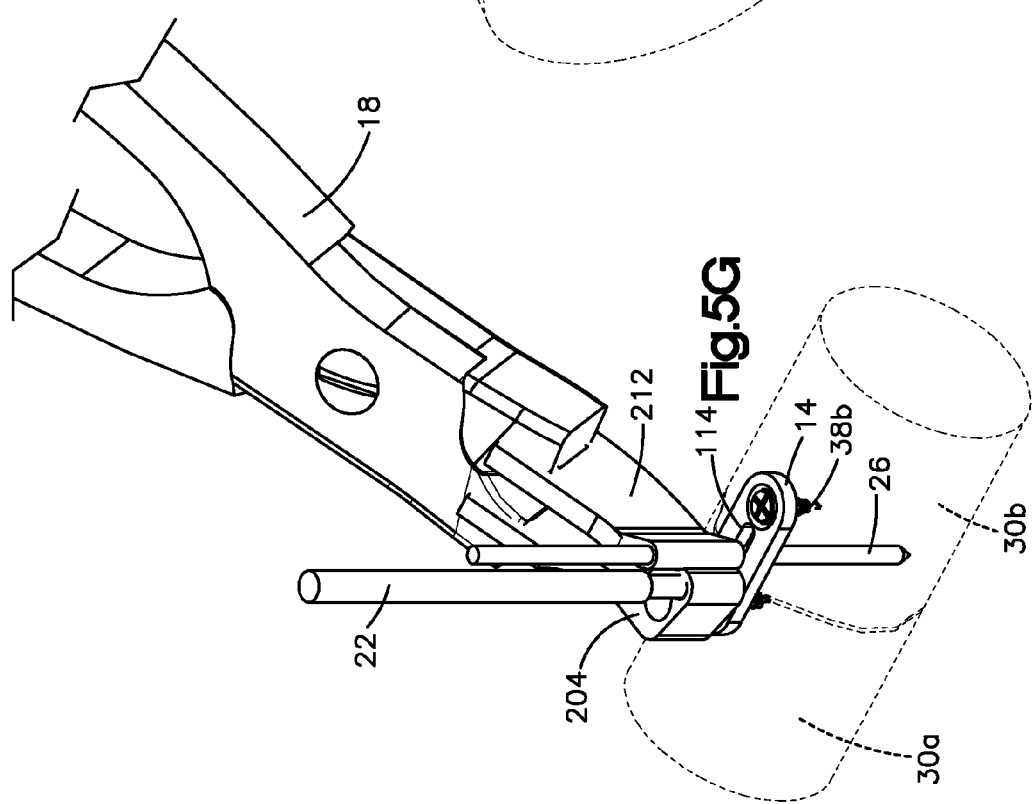

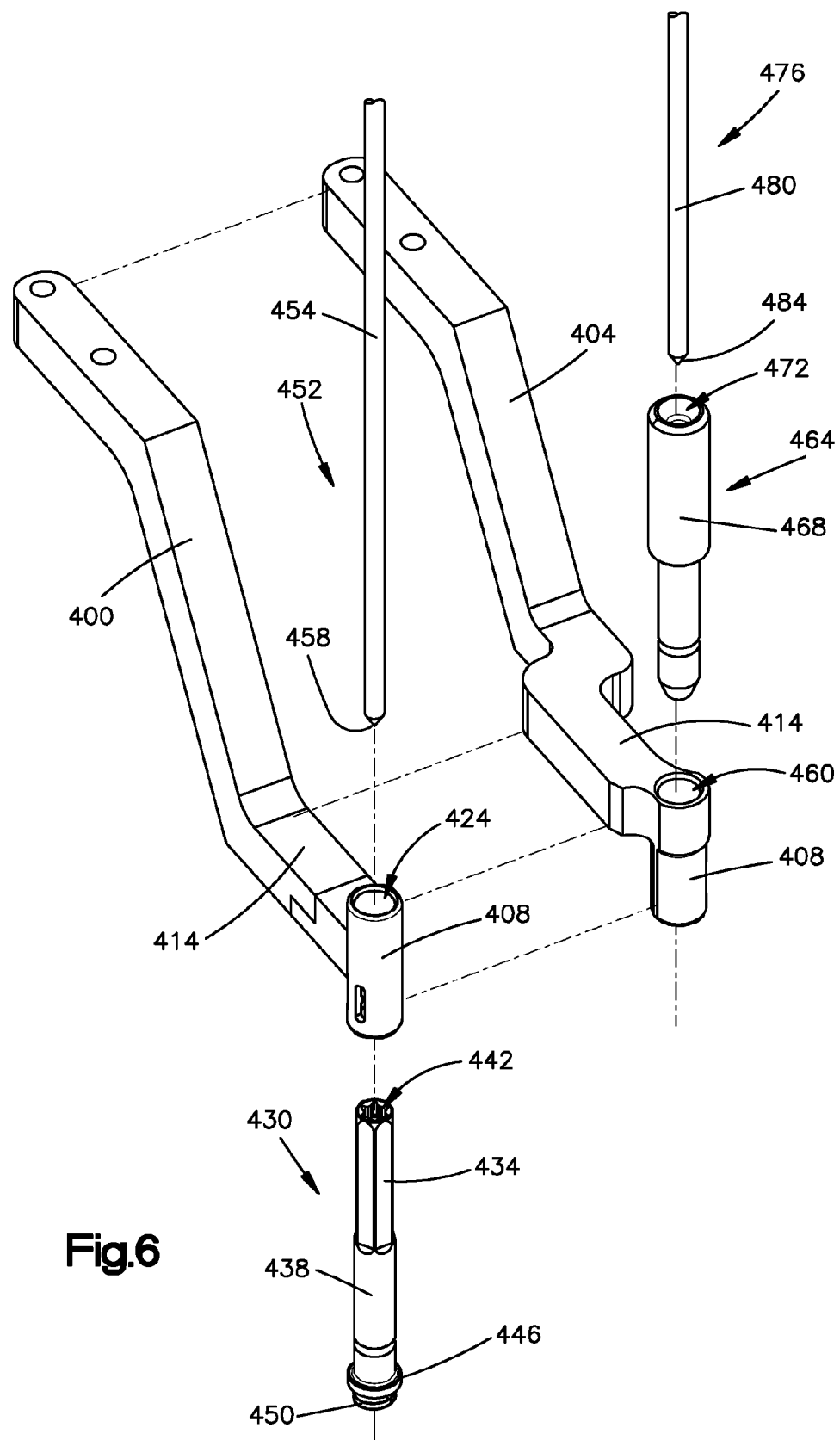

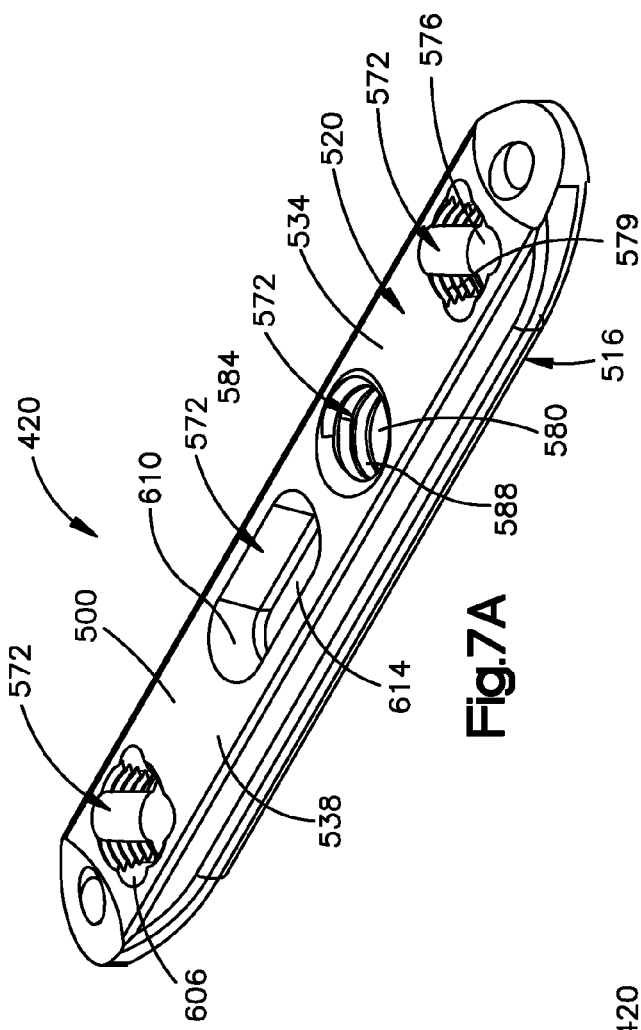
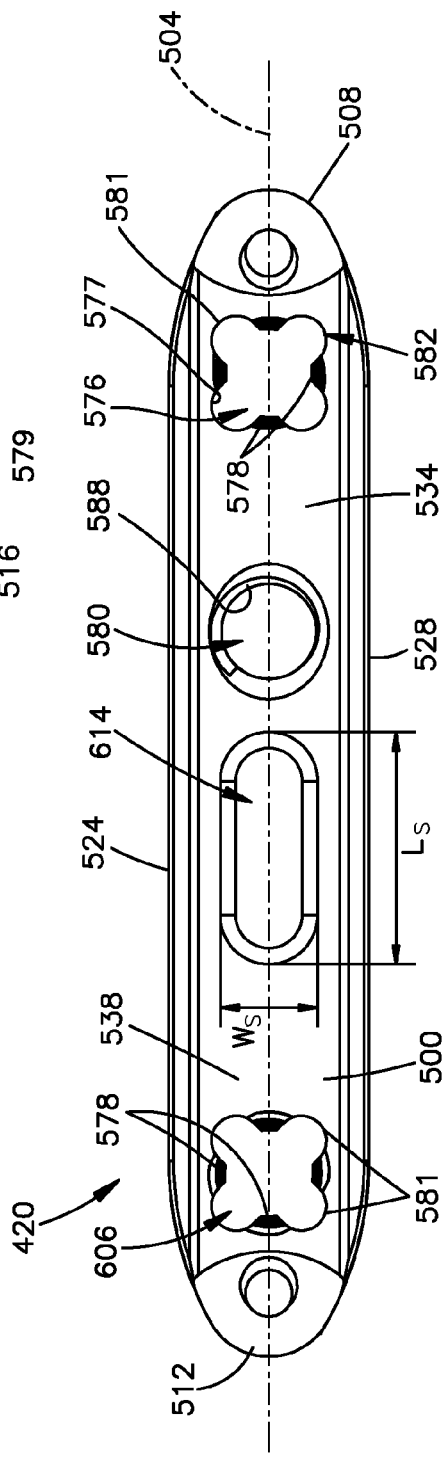
Fig.7A
Fig.7B

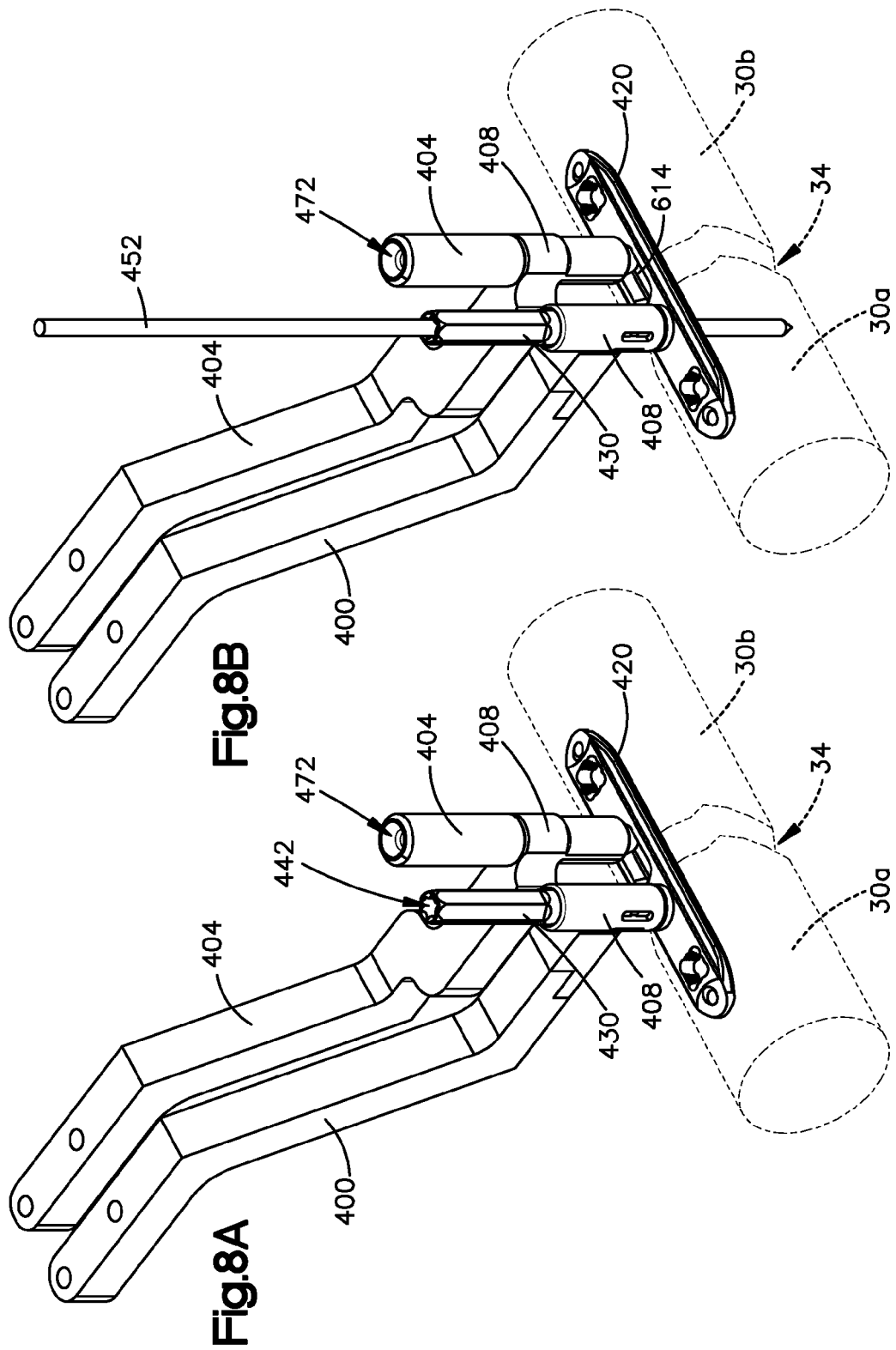

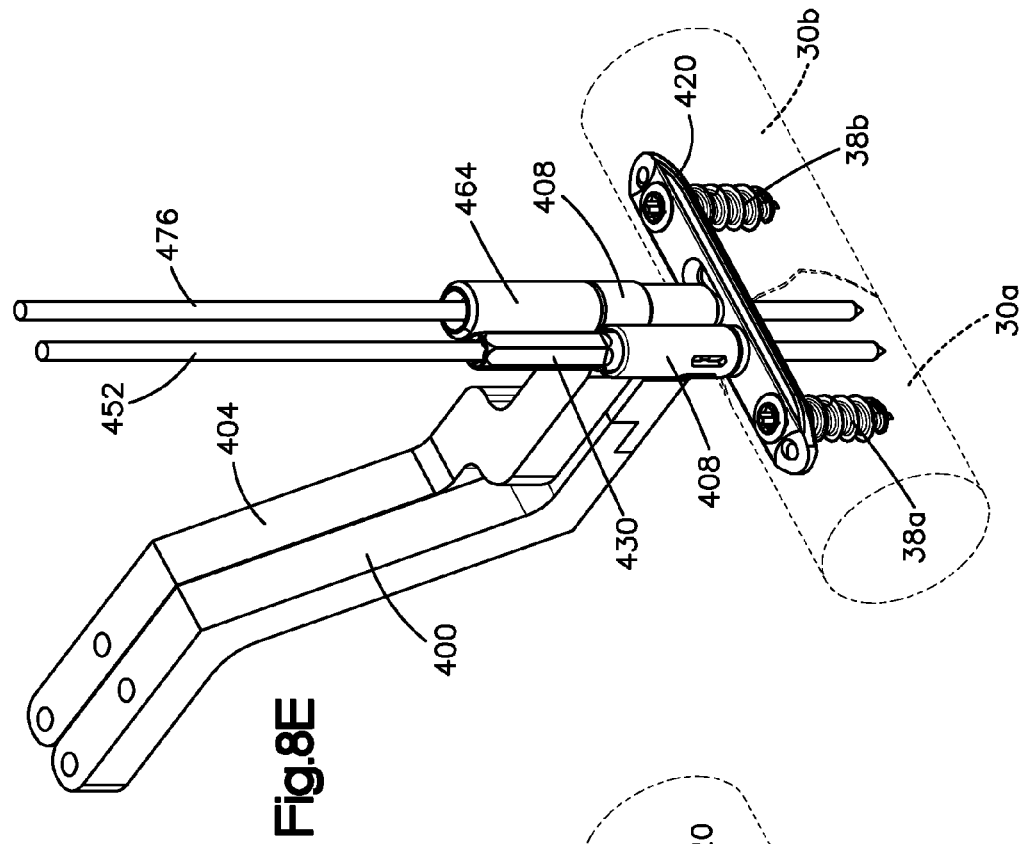
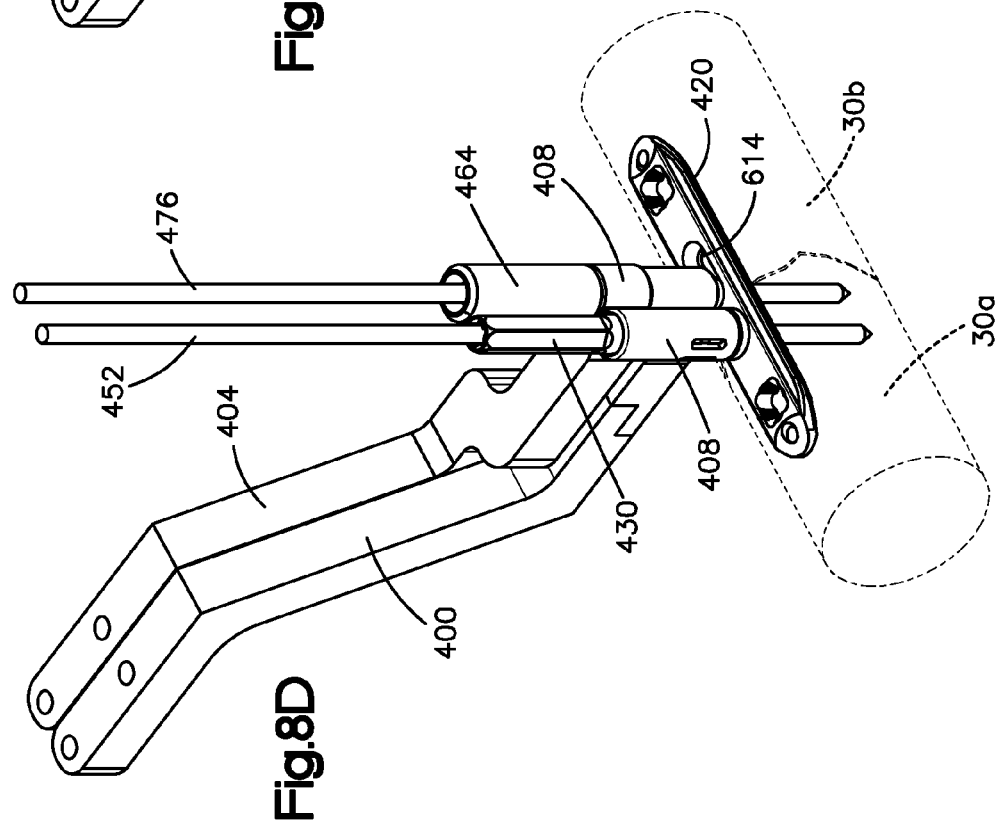

BONE FIXATION SYSTEMS AND METHODS OF USE

CROSS REFERENCE TO RELATED APPLICATIONS

This is a continuation of U.S. patent application Ser. No. 13/095,162 filed Apr. 27, 2011, which claims the benefit of U.S. Provisional Application Ser. No. 61/328,347 filed Apr. 27, 2010, and also claims the benefit of U.S. Provisional Application Ser. No. 61/328,381 filed Apr. 27, 2010, the contents of each of which are incorporated herein by reference in their entirety.

BACKGROUND

In order to restore the correct position of first and second bone segments of a fractured bone it is often desirable to close or reduce a gap between the two bone segments. Similarly, in the case of an arthrodesis, where two separate bones have to be fused, a gap has to be closed. Commonly surgical compression forceps are used to displace the bone segments towards each other. After reducing the fractured bone a bone plate is fixed to the bone segments to hold the bone segments in place.

Because the bone plate is fixed to the bone segments in the very same region as the compression forceps are attached to the bone segments, it is often difficult to retain the reduced bone segments in position since the compression forceps and the bone implant interfere with each other.

SUMMARY

In one embodiment, a bone fixation system may be configured to move at least one of a first bone segment and a second bone segment relative to the other. The first and second bone segments may be separated by a bone gap. The system may include a first lever and a second lever pivotally coupled to the first lever. The first lever may include a first handle, a first jaw extending from the first handle, and an aperture extending through the first jaw. The aperture may be configured to receive a fixation element to thereby fixedly couple the first lever to a bone plate. The second lever may include a second handle, a second jaw extending from the second handle, and an aperture extending through the second jaw. The aperture may be configured to receive a temporary fixation element to operatively couple the second lever to the second bone segment such that when in use, the temporary fixation element is capable of translating relative to the bone plate so as to allow reduction of the first and second bone segments.

The forceps may be sold as part of a kit. The kit may include at least one bone fixation plate having a first body portion and a second body portion. The first body portion may define at least two apertures. A first aperture of the at least two apertures is configured to receive a bone anchor to thereby affix the bone fixation plate to the first bone segment. A second aperture of the at least two apertures may include a coupler configured to releasably couple the bone fixation plate to the forceps. The second body portion may define at least two apertures. A first aperture of the at least two apertures may be configured to receive a bone anchor to thereby affix the bone fixation plate to the second bone segment. A second aperture of the at least two apertures may include a slot having a lateral dimension and a longitudinal dimension that is greater than the lateral dimension. The slot may be configured to receive a temporary fixation element such that the temporary fixation element is longitudinally translatable within the slot.

Also disclosed is a method of fixing a bone plate having a first body portion and a second body portion to first and second bone segments. The first and second bone segments may be disposed in a relative position in relation to each other and may be separated by a bone gap. According to the method a bone plate may be aligned with the first and second bone segments such that a first plurality of apertures extending through the first body portion of the bone plate are aligned with the first bone segment and a second plurality of apertures extending through the second body portion of the bone plate are aligned with the second bone segment. A forceps having first and second jaws may be coupled to the bone plate either after or before the bone plate is aligned, by inserting a fixation element through the first jaw and into a first aperture of the first plurality of apertures that extend through the first body portion of the bone plate. The first body portion of the bone plate may be affixed to the first bone segment with a bone anchor. A temporary fixation element may be coupled to the second bone segment such that the temporary fixation element extends through the second jaw of the forceps and through an aperture of the second plurality of apertures that extend through the second body portion of the bone plate. By actuating the forces, at least the temporary fixation element is biased so as to translate relative to the bone plate, thereby adjusting the relative positions of the first and second bone segments in relation to each other.

BRIEF DESCRIPTION OF THE DRAWINGS

The foregoing summary, as well as the following detailed description of preferred embodiments of the application, will be better understood when read in conjunction with the appended drawings. For the purposes of illustrating the forceps and bone plates of the present application, there is shown in the drawings preferred embodiments. It should be understood, however, that the application is not limited to the precise systems and methods shown. In the drawings:

FIG. 2A is a perspective view of the bone fixation plate illustrated in FIG. 1, the bone fixation plate including a plurality of apertures, two of the apertures are configured to receive bone anchors, one aperture is configured to receive the fixation element so as to fixedly couple the forceps to the bone fixation plate, and one aperture defines a slot and is configured to receive the temporary fixation element;

FIG. 2B is a top plan view of the bone fixation plate shown in FIG. 2A;

FIG. 4B is a top perspective view of the first and second jaws of the lever shown in FIG. 4A positioned over the bone fixation plate shown in FIG. 2A, the first aperture of the first jaw receiving the fixation element so as to fixedly couple the first jaw to the bone fixation plate, and the aperture of the second jaw receiving the temporary fixation element;

FIG. 4C is a bottom perspective view of the first and second jaws shown in FIG. 4B;

FIG. 5A is a perspective view of the bone fixation system shown in FIG. 1 with the first jaw fixedly coupled to the bone fixation plate by the fixation element, the bone fixation plate positioned against first and second bone segments that define a bone gap;

FIG. 5B is a perspective view of a first bone anchor being inserted through one of the apertures defined by the first jaw so as to affix the bone fixation plate to the first bone segment;

FIG. 5C is a perspective of the bone fixation plate affixed to the first bone segment with the first bone anchor;

FIG. 5D is a perspective view of the bone fixation system shown in FIG. 5C, with the second jaw positioned over the bone fixation plate such that the aperture of the second jaw is aligned with the slot of the bone fixation plate;

FIG. 5E is a perspective view of the bone fixation system shown in FIG. 5D, with the temporary fixation element extending through the aperture of the second jaw and through the slot of the bone fixation plate so as to couple the second jaw to the second bone segment;

FIG. 5F is a perspective view of the bone fixation system shown in FIG. 5E, after the forceps have been compressed and the first and second bone segments have been translated so as to reduce the bone gap;

FIG. 5G is a perspective view of the bone fixation system shown in FIG. 5F, after a second bone anchor has affixed the bone fixation plate to the second bone segment;

FIG. 5H is a perspective view of the bone fixation plate affixed to the first and second bone segments, after the forceps and temporary fixation element have been removed;

FIG. 6 is an exploded view of a bone fixation system in accordance with another embodiment, the bone fixation system including a forceps having a first jaw and a second jaw, a fixation element configured to fixedly couple the first jaw of the forceps to a bone fixation plate, and a pair of temporary fixation elements configured to operatively couple the first and second jaws of the forceps to first and second bone segments;

FIG. 7A is a perspective view of bone fixation plate constructed in accordance with another embodiment, the bone fixation plate having a plurality of apertures, two of the apertures configured to receive bone anchors, one of the apertures configured to receive a fixation element so as to fixedly couple the forceps to the bone fixation plate, and one of the apertures defines a slot and is configured to receive one of the temporary fixation elements;

FIG. 7B is a top plan view of the bone fixation plate shown in FIG. 7A;

FIG. 8A is a perspective view of the forceps shown in FIG. 6 fixedly coupled to the bone fixation plate shown in FIG. 7A with the fixation element, the bone fixation plate positioned against first and second bone segments that are separated by a bone gap;

FIG. 8B is a perspective view of the first temporary fixation element extending through the fixation element and into the first bone segment so as to couple the first jaw to the first bone segment;

FIG. 8D is a perspective view of the bone fixation system shown in FIG. 8C, after the forceps have been compressed and the first and second bone segments have been translated so as to reduce the bone gap; and FIG. 8E is a perspective view of the bone fixation system shown in FIG. 8E, after first and second bone anchors have affixed the bone fixation plate to the first and second bone segments.

DETAILED DESCRIPTION

Figure 1:
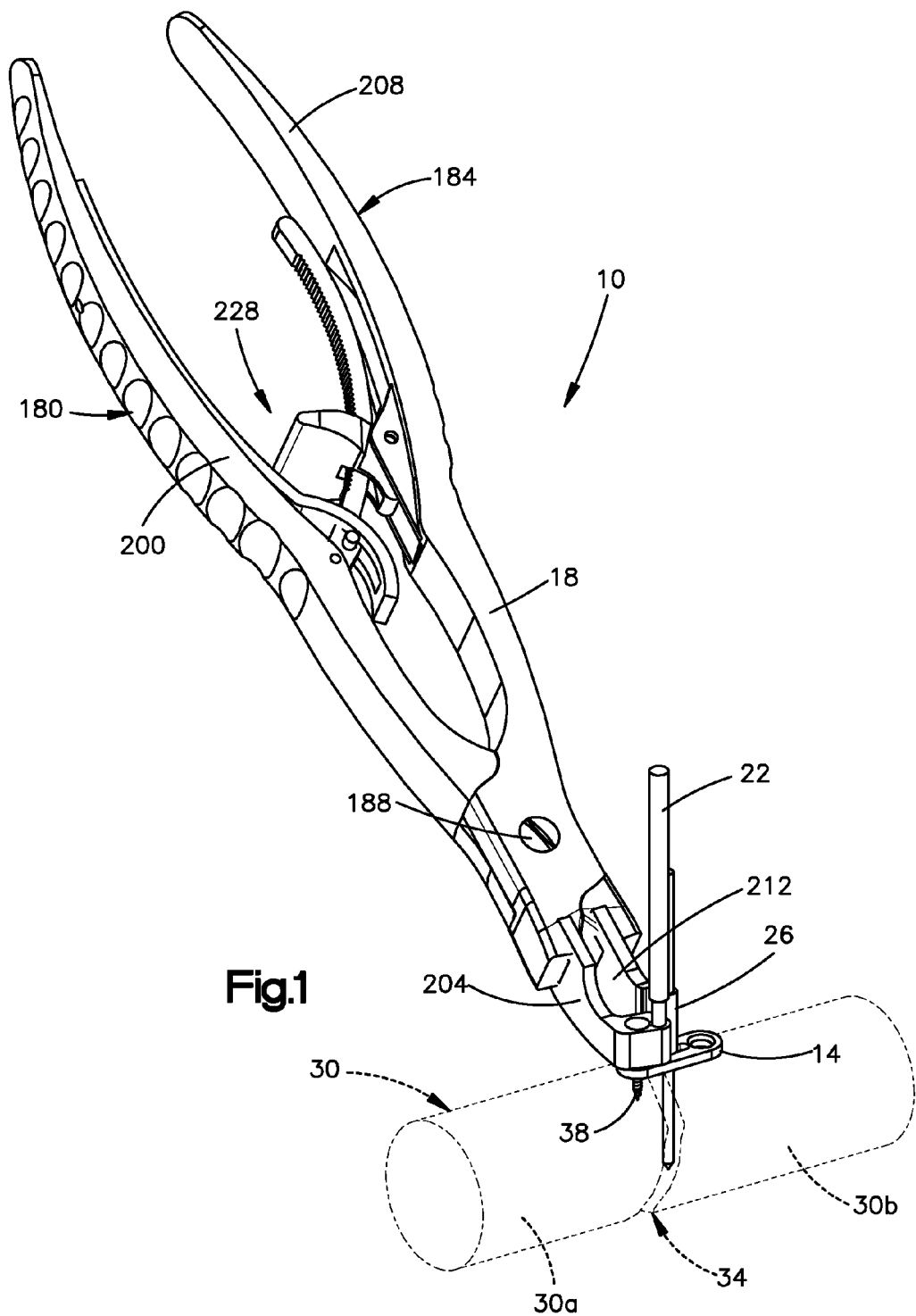
FIG. 1 is a perspective view of a bone fixation system constructed in accordance with one embodiment and operatively coupled to a pair of schematically illustrated bone segments separated by a bone gap, the bone fixation system including a bone fixation plate, a forceps fixedly coupled to the bone plate with a fixation element, and a temporary fixation element that extends through both the forceps and the bone plate.

Referring to FIG. 1, a bone fixation system 10 includes a bone fixation plate 14, a temporary fixation element illustrated as a K-wire 26, and a forceps 18. The bone fixation plate 14 can be operatively coupled to an underlying bone 30 having bone segments 30a and 30b that are separated by a bone gap 34. The bone fixation system 10 further includes a plurality of (e.g. at least two) bone fixation elements or bone anchors 38 that secure the bone fixation plate 14 to the underlying bone 30 on opposed sides of the bone gap 34. The bone anchors 38 are illustrated as bone screws, though it should be understood that any bone anchor capable of affixing the bone fixation plate 14 to the underlying bone 30 may be used. The forceps 18 is configured to be operatively coupled between the bone fixation plate 14 and the K-wire 26 so as to approximate the bone gap 34 during operation. For instance, the forceps 18 can include a pair of jaws 204 and 212 and a fixation element 22 that is configured to be fixedly coupled between the bone fixation plate 14 and one of the jaws 204 and 212. The other of the jaws 204 and 212 can be fixedly coupled to the K-wire 26 which extends through an elongate K-wire slot 114 (see FIG. 2A) of the bone fixation plate 14 and into the corresponding bone segment 30b. One of the bone anchors 38 can couple the bone fixation plate 14 to the opposed bone segment 30a. Accordingly, the forceps 18 is configured to compress the jaws 204 and 212 toward each other so as to apply a biasing force to at least one or both of the corresponding fixation element 22 and K-wire 26, thereby causing at least one of the bone fixation element 22 and the K-wire 26 to travel toward the other so as to approximate the bone gap 34. The bone gap 34 can be a fracture created by a traumatic event, an osteotomy, or can be the result of debridement of a joint of two discrete bones to be joined in an arthodesis.

The bone fixation plate 14 is placed against or in proximity with the underlying bone 30 and is fixedly coupled to the forceps 18. A first bone anchor 38a may affix the bone fixation plate 14 to the first bone segment 30a. The K-wire 26 may then be inserted through the forceps 18, through the bone fixation plate 14, and into the second bone segment 30b. By applying a force to the forceps 18 at least one of or both of the bone segments 30a and 30b may be translated, thereby adjusting the relative positions of the bone segments 30a and 30b in relation to each other. For instance, the forceps 18 can apply a compressive force that brings at least one or both of the bone segments 30a and 30b toward the other, thereby reducing the bone gap 34 to promote union of the bone segments 30a and 30b. It should be understood that the forceps 18 may also provide a distractive force so as to urge one of or both of the bone segments 30a and 30b away from the other, thereby distracting the bone gap 34. The bone fixation plate 14 can be geometrically configured for fixation to the bone 30, which can be the forefoot, midfoot, hind-foot, distal tibia, or any bone in the human body as desired, either in vivo or ex vivo. The bone fixation plate 14 can alternatively be fixed in the manner described above to any suitable non-human animal body bone, in vivo or ex vivo.

The bone fixation system 10 and components of the bone fixation system 10 can be made from any suitable biocompatible material, such as titanium, including titanium alloys, stainless steel, ceramics, or polymers such as polyetheretherketone (PEEK), cobalt chromium molybdenum (CoCrMo) with a porous plasma-sprayed titanium coating, or any suitable alternative material as desired.

Referring now to FIGS. 2A and 2B, the bone fixation plate 14 can be made in different shapes and sizes for use in a wide variety of clinical applications. The bone fixation plate 14 is elongate along a longitudinal direction L, defines a width along a lateral direction A that is perpendicular or substantially perpendicular to the longitudinal direction L, and a thickness along a transverse direction T that is perpendicular or substantially perpendicular to both the longitudinal direction L and the lateral direction A. In this regard, it should be appreciated that the various directions can extend along directions that are 90° angularly offset from each other, or anywhere within the range of approximately 45° and approximately 90° angularly offset from each other.

The bone fixation plate 14 includes a bone plate body 40 that extends substantially along a central longitudinal axis 42, and defines a proximal end 44 and a distal end 48 opposite the proximal end 44 along the longitudinal axis 42. The plate body 40 further defines a bone facing inner surface 52 and an opposed outer surface 56 spaced from the inner surface 52 along the transverse direction T. The plate body 40 further defines opposed side surfaces 58 and 60 that are spaced from each other along the lateral direction A.

As shown in FIGS. 2A and 2B, the plate body 40 includes a first body portion 64 and an adjoining second body portion 68. The first and second body portions 64 and 68 may be integrally formed (i.e. one single member) and may be configured to contour to the underlying bone 30. In particular, the bone fixation plate 14 is configured to span the bone gap 34 such that the first body portion 64 at least partially contours to the first bone segment 30a and the second body portion at least partially contours to the second bone segment 30b.

With continuing reference to FIGS. 2A-2B, the bone plate 14 defines a plurality of apertures 72 that extend transversely through the plate body 40, from the bone-facing inner surface 52 through to the outer surface 56. In particular, the first body portion 72 of the plate body 40 defines at least two apertures 72, and the second body portion 68 of the plate body 40 defines at least two apertures 72. In the illustrated embodiment, the first body portion 64 defines three apertures 72 and the second body portion 68 defines two apertures 72, though it should be understood that any number of apertures 72 may extend through the first and second body portions 64 and 68.

As shown, the first body portion 64 of the bone fixation plate 14 includes a first or bone anchor aperture 76 that is configured to receive a bone anchor 38, and a second fixation element receiving aperture 80 that is configured to receive the fixation element 22. The first aperture 76 extends through the bone fixation plate 14 and is configured to receive the bone anchor 38 so as to affix the first body portion 64 of the bone fixation plate 14 to the first bone segment 30a. The first aperture 76 is positioned between the proximal end 44 and the second aperture 80. The first aperture 76 may include a conical interior thread that tapers toward the bone-facing inner surface 52. The tapered first aperture 76 may help prevent the bone anchor 38 from backing out after the bone anchor 38 has affixed the bone fixation plate 14 to the first bone segment 30a.

As shown in FIGS. 2A and 2B, the second aperture 80 also extends through the bone fixation plate 14 and includes a coupler 84 that is configured to be engaged by the fixation element 22 so as to fixedly couple the forceps 18 to the bone fixation plate 14. In the illustrated embodiment, the coupler 84 includes internal threads 88 that are configured to be engaged by external threads 318 defined by the fixation element 22 (see e.g. FIG. 4B). It should be understood, however, that the coupler 84 may include structure other than the internal threads 88. For example, the coupler 84 may define a snap on mounting. Moreover, while the fixation element 22 is illustrated as a pin, it should be understood that the fixation element 22 may be any structure capable of fixedly coupling the forceps 18 to the bone fixation plate 14.

As shown, the first body portion 64 may further include a positioning element 96 that is configured to be engaged by a positioning element defined by the forceps 18 so as to align the forceps 18 and the bone fixation plate 14 with a defined position and to prevent rotation of the bone fixation plate 14 relative to the forceps 18. As shown, the positioning element is configured as a bore or third aperture 102 that extends at least partially into the plate body 40. As illustrated, the third aperture 102 may extend completely through the plate body 40.

As shown, the second aperture 80 and the third aperture 102 are offset and aligned in the lateral direction A on opposed sides of the central axis 42. Both apertures 80 and 102 are located distally from the first aperture 76 but extend through the first body portion 64 of the bone fixation plate 14.

As shown, the second body portion 68 of the bone fixation plate 14 includes a first or bone anchor aperture 106 that is configured to receive a bone anchor 38, and a second aperture 110 that is configured to receive the K-wire 26. The first aperture 106 extends through the bone fixation plate 14 and is configured to receive the bone anchor 38 so as to affix the second body portion 68 of the bone fixation plate 14 to the second bone segment 30b. The bone anchor aperture 106 is positioned between the distal end 48 and the second aperture 110. The first aperture 106 may include a conical interior thread that tapers toward the bone-facing inner surface 52. The tapered first aperture 106 may help prevent the bone anchor 38 from backing out after the bone anchor 38 has affixed the bone fixation plate 14 to the second bone segment 30b.

As shown in FIGS. 2A and 2B, the second aperture 110 also extends through the bone fixation plate 14 and defines a K-wire slot 114 that is configured to receive the K-wire 26 such that the K-wire 26 can engage or otherwise extend into the second bone segment 30b. As shown in FIG. 2B, the K-wire slot 114 has a lateral width Ws and a longitudinal length Ls that is substantially greater than the lateral width Ws. The lateral width Ws of the K-wire slot 114 may be substantially equal to the diameter of the K-wire 26 so as to prevent lateral misalignment of the bone fixation plate 14 during the compression of the bone segments, while at the same time allowing the K-wire 26 to translate within the slot 114 along the longitudinal direction L. The longitudinal length Ls of the K-wire slot 114 may be a length that allows the K-wire 26 and thus the second bone segment 30b to translate toward the first bone segment 30a upon compression of the forceps 18. It should be understood, however, that the second aperture 110 may have any dimension desired. For example, the second aperture 110 may be a K-wire slot having a lateral width that is greater than the diameter of the K-wire or the second aperture 110 may have a dimension that receives other structure so long as the structure is capable of translating within the aperture.

As shown in FIGS. 2A and 2B, the second aperture 80 of the first body portion 64 and the second aperture 110 of the second body portion 68 are spaced from each other along the longitudinal direction L by a width $W_B$. The second apertures 80 and 110 are separated such that a solid piece of the bone plate body 40 is disposed between the two apertures.

Figure 3A:
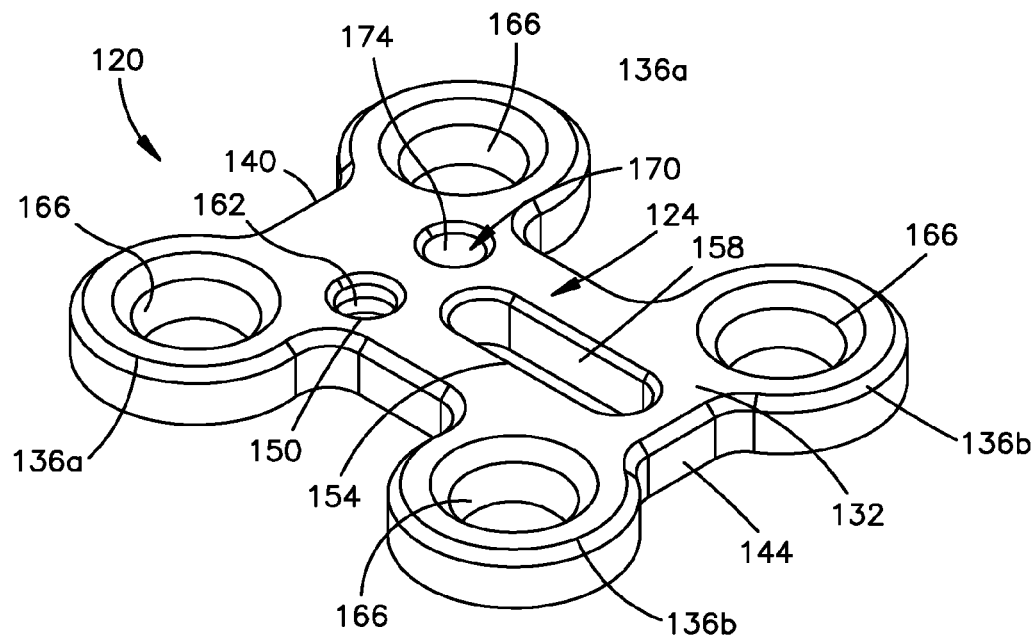
FIG. 3A is a perspective view of a bone fixation plate constructed similar to the bone plate illustrated in FIG. 2A, but in accordance with another embodiment.
Figure 3B:
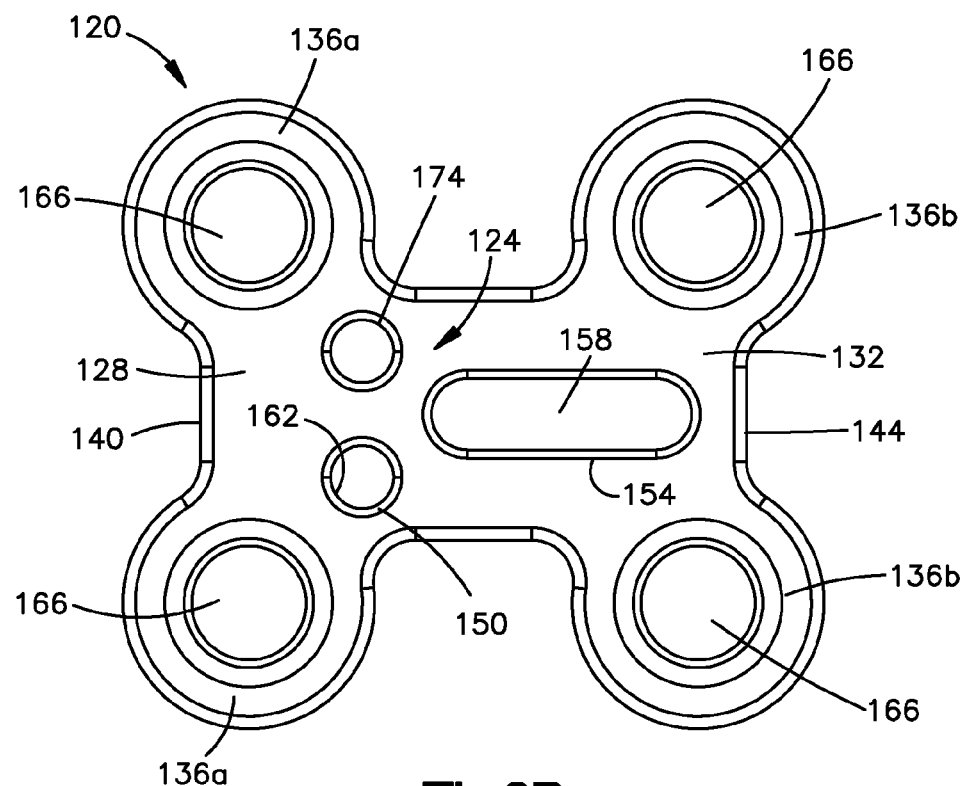
FIG. 3B is a top plan view of the bone fixation plate shown in FIG. 3A.

Referring to FIGS. 3A and 3B, an alternatively constructed bone fixation plate 120 includes a bone plate body 124 that defines a first body portion 128 and a second body portion 132. The bone plate body 124 further defines a first pair of laterally opposed flared regions 136a that extend distally and laterally outward from a proximal end 140 of the first body portion 128, and a second pair of laterally opposed flared regions 136b that extend proximally and laterally outward from a distal end 144 of the second body portion 132. The first and second body portions 128 and 132, and first and second flared regions 136a and 136b impart a substantial X-shape to the bone plate body 124.

Similar to the bone fixation plate 14, the bone fixation plate 120 includes a plurality of apertures that extend through the bone plate body 124. In particular, the first body portion 128 includes an aperture 150 that is configured to receive the fixation element so as to fixedly couple the forceps 18 to the bone fixation plate 120, and the second body portion 132 includes an aperture 154 that defines a K-wire slot 158 and is configured to receive the K-wire 26. As shown, the aperture 150 includes a coupler 162, which in the illustrated embodiment is internal threads that allow the bone fixation plate 120 to be fixedly coupled to the forceps 18. To affix the bone fixation plate 120 to the underlying bone each flared region 136a and 136b defines a respective bone anchor aperture 166 that is configured to receive a respective bone anchor.

Also similar to the bone fixation plate 14, the first body portion 128 of the bone fixation plate 120 may further include a positioning element 170 that is configured to be engaged by a positioning element defined by the forceps 18 so as to align the forceps 18 and the bone fixation plate 120 with a defined position and to prevent rotation of the bone fixation plate 120 relative to the forceps 18. As shown, the positioning element 170 is configured as a bore or third aperture 174 that extends at least partially into the plate body 124. As illustrated, the third aperture 174 extends completely through the plate body 124.

Now referring to FIGS. 1 and 4A-4F, the forceps 18 includes a first lever 180 and a second lever 184 pivotally connected together at a joint 188 (i.e. a pin inserted into an aperture defined by both levers), which divides the levers 180 and 184 between a proximal portion 192 and an opposing distal portion 196. The proximal portion 192 of the first lever 180 defines a first handle 200, and the distal portion 196 of the first lever defines a first jaw 204 that extends distally from the first handle 200. Similarly, the proximal portion 192 of the second lever 184 defines a second handle 208, and the distal portion 196 of the second lever 184 defines a second jaw 212. The first and second handles 200 and 208 can present outer grip surfaces 220, while the first and second jaws 204 and 212 define engagement members 224. The forceps 18 includes a fixation element 22 that is configured to be fixedly coupled to the bone fixation plate 14, such that a select one of the engagement members 224 can be fixedly coupled to the fixation element 22 so as to fixedly couple the forceps to the bone fixation plate 14. Accordingly, the select engagement member 224 is configured to apply a force against the fixation element 22, and thus to the bone fixation pate 14, along a direction from the fixation element 22 toward the K-wire slot 114. It should thus be appreciated that when the K-wire slot 114 receives a temporary fixation element (such as K-wire 26), and the other of the engagement members 224 is operatively coupled to the K-wire 26, movement of the first and second jaws 204 and 212 toward each other approximates the bone gap 28 (see, e.g., FIG. 1).

Figure 4A:
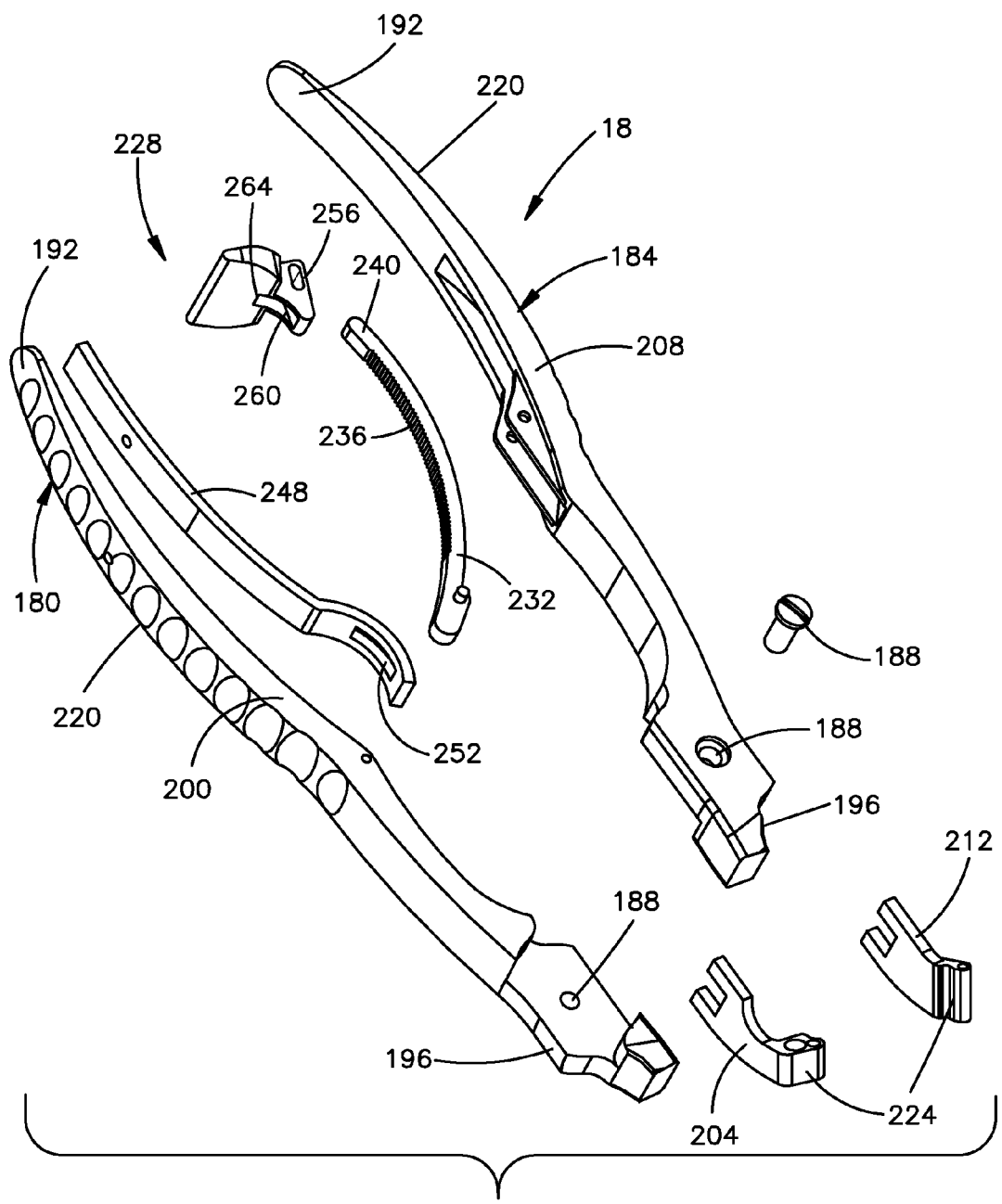
FIG. 4A is an exploded view of the forceps shown in FIG. 1, the forceps including a first lever and a second lever pivotally coupled to the first lever, the first and second levers each having a handle, and a jaw extending from the handle, a first jaw of the first lever including an aperture configured to receive a bone anchor, and an aperture configured to receive the fixation element so as to fixedly couple the first jaw to the bone fixation plate, and a second jaw of the second lever including an aperture configured to receive the temporary fixation element such that the temporary fixation element extends through the aperture and into the slot of the bone fixation plate.

The levers 180 and 184 are pivotally connected, such that when the handles 200 and 208 are brought together, the engagement members 224 are likewise brought together, and when the handles 200 and 208 are moved apart, the engagement members 224 are likewise moved apart. Referring to FIG. 4A, the forceps 18 include a ratchet 228 that causes the levers 180 and 184 to move together incrementally. For instance, in the illustrated embodiment the first lever 180 carries a rack 232 that carries a plurality of teeth 236 extending out from a rack body 240. In accordance with the illustrated embodiment, the rack 232 extends from the proximal portion 192 of the first lever 180, and is pivotally connected to the lever 180 at a joint 244. The first arm 180 also carries a guide 248 that defines a guide channel 252 that receives the rack 232.

The second lever 184 carries a pair of opposed channel walls 256 that define a channel 260 therebetween. The channel 260 receives the rack 232 which is directed into the channel 260 by the guide 248, such that the rack 232 is translatable within the channel 260. The channel walls 256 further carry at least one tooth 264 that can be spring-biased into engagement with the teeth 236 of the rack 232. The tooth 264 and the teeth 236 can be configured such that the tooth 264 rides over the teeth 236 as the handles 200 and 208 are brought together. The spring force provides resistance as the tooth 264 rides along each tooth 236, biases the tooth 264 into the valleys between the adjacent teeth 236 so as to provide tactile feedback as the handles 200 and 208, and thus the engagement members 224 incrementally close. The teeth 236 and 264 can further be configured such that interference prevents the tooth 264 from riding along the teeth 236 when a separation force is applied to the handles 200 and 208, if desired. The tooth 264 can include an engagement surface that can be depressed by a user against the spring force to bring the tooth 264 out of engagement with the teeth 236 so as to allow for separation of the handles 200 and 208, and thus separation of the engagement members 224. In another embodiment, the teeth 236 and 264 can be configured such that the tooth 236 incrementally rides along the teeth 264 in the manner described above both when the handles 200 and 208, and thus the engagement members 224 are separated, and when the handles 200 and 208, and thus the engagement member 224 are brought together.

As shown in FIG. 4A, the handles 200 and 208, and the jaws 204 and 212 may be separate components that are coupled together. It should be understood, however, that the handles 200 and 208, and the jaws 204 and 212 may be integrally formed such that the levers 180 and 184 each define a single arm.

As best shown in FIGS. 4B and 4C, the engagement member 224 of the first jaw 204 may be configured to be fixedly coupled to the bone fixation plate 14. As shown, the first jaw 204 includes a first or fixation element receiving aperture 300 that extends transversely through the engagement member 224, and a second or access aperture 304 that extends transversely through the engagement member 224, such that central axes of the first and second apertures 300 and 304 are generally perpendicular to the outer surface 56 of the bone fixation plate 14. As shown in FIGS. 4B-4D, and 4F, the first aperture 300 is configured to receive the fixation element 22 such that the fixation element 22 extends completely through the first aperture 300 and engages the second aperture 80 of the bone fixation plate 14 so as to fixedly couple the first jaw 204 to the bone fixation plate 14. As shown, the fixation element 22 is a pin having a pin body 310 and a coupler 314 extending from a distal end of the pin body 310. In the illustrated embodiment, the coupler 314 defines external threads 318 that are configured to engage the internal threads 88 of the second aperture 80 of the bone fixation plate 14. As best shown in FIG. 4F, the coupler portion 314 of the pin has a dimension that is less than the dimension of the proximal portion of the pin body 310, to thereby define a shoulder at the junction of the proximal portion and coupling portion of the pin body 310. The first aperture 300 includes a dimension such as a diameter that is substantially equal to the dimension or diameter of the fixation element 22 so that when the fixation 22 fixedly couples the first jaw 204 to the bone plate 14, the bone plate 14 cannot move relative to the first jaw 204, though it should be understood that the aperture 300 may have any dimension as desired. When the coupler 314 is inserted through the aperture 300 and is fixedly coupled to the bone fixation plate 14, the first jaw 204 will be trapped between the shoulder of the fixation element 22 and the bone fixation plate 14 to thereby fixedly couple the first jaw 204 to the bone fixation plate 14.

As shown in FIGS. 4B and 4C, the second aperture 304 is positioned adjacent the first aperture 300 and is configured to receive or otherwise provide an access path for a drill and/or the bone anchor 38a to pass through to the first aperture 76 of the bone fixation plate 14 so that the bone anchor 38a can affix the first body portion 64 of the bone fixation plate 14 to the first bone segment 30a. The second aperture 304 may include any dimension, such as a diameter, as desired, so long as the dimension allows the bone anchor 38a to pass therethrough.

As shown in FIGS. 4C and 4F, the first jaw 204 further includes a positioning element 322 that extends from a bottom surface of the engagement member 224 and toward the bone plate 14. As shown, the positioning element 322 defines a cylindrical rod or peg that is configured to engage or otherwise mate with the aperture 96 of the bone fixation plate 14. When the peg 322 is engaged with the aperture 96, and the fixation element 22 is engaged with the aperture 80, the bone fixation plate 14 will be fixed relative to the first jaw 204 in a known defined position. That is, the bone fixation plate 14 may be properly aligned with the first jaw 204, and may be prevented from rotating.

As shown in FIGS. 4B-4E, the second jaw 212 includes a temporary fixation element receiving aperture 326 that extends transversely through the engagement member 224 of the second jaw 212 such that a central axis of the aperture 326 is generally perpendicular to the outer surface 56 of the bone fixation plate 14. The aperture 326 is sized to receive the temporary fixation element 26 so as to guide the temporary fixation element 26 through the second jaw 212 and into the slot 114 of the bone fixation plate 14. As shown in FIG. 4E, the temporary fixation element 26 includes a distal end 330 that is configured to engage or otherwise extend into the second bone segment 30b so as to operatively couple the second jaw 212 to the second bone segment 30b. Therefore, when the second jaw 212 is translated the temporary fixation element 26 and thus the second bone segment 30b will translate along with the second jaw 212. The aperture 326 may include a dimension, such as a diameter, that is substantially equal to the dimension or diameter of the temporary fixation element 26, such that when the aperture 326 has received the temporary fixation element 26, the temporary fixation element 26 will not move relative to the second jaw 212.

Figure 4D:
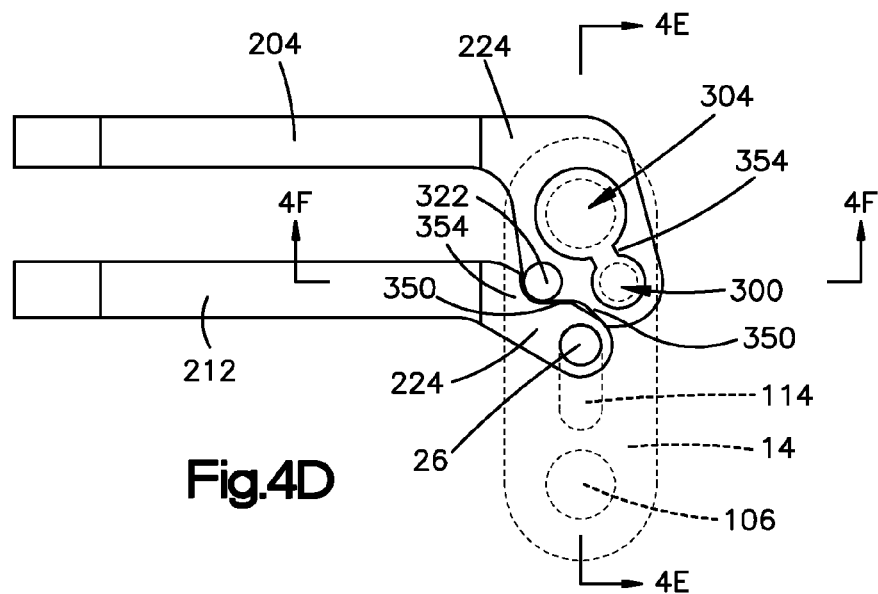
FIG. 4D is a bottom plan view of the first jaw fixedly coupled to the bone fixation plate, which is shown in phantom lines.
Figures 4E, 4F:
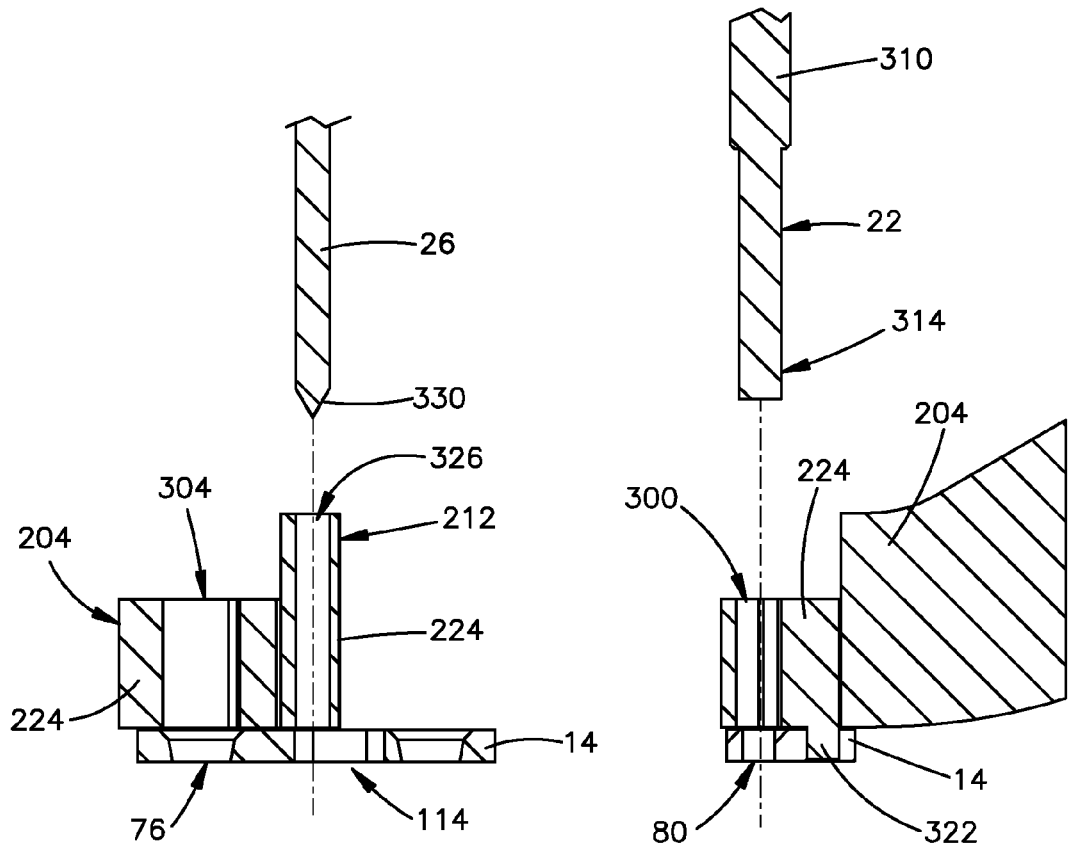
FIG. 4E is a sectional side elevation view of the first and second jaws through the line 4E-4E shown in FIG. 4D.
FIG. 4F is a sectional side elevation view of the first jaw through the line 4F-4F shown in FIG. 4D.

As best shown in FIG. 4D, the engagement members 224 define internal or opposing surfaces 350 that are shaped to allow the first and second jaws 204 and 212 to compress the bone segments 30a and 30b without interference from each other. In particular each inner surface 350 defines a recess 354 that provides clearance for the opposing engagement member 224. As shown in FIG. 4D, when fully compressed the internal surfaces 350 of the engagement members 224 substantially conform to each other such that they can abut each other.

In operation and in reference to FIGS. 5A-5H, the bone plate 14 is aligned with and placed over or on the underlying bone 30 such that the bone anchor aperture 76 of the first body portion 64 of the plate 14 is aligned with the first bone segment 30a, and the bone anchor aperture 106 of the second body portion 68 of the plate 14 is aligned with the second bone segment 30b. Either prior to or after the bone fixation plate 14 has been aligned with the bone 30, the forceps 18 may be fixedly coupled to the bone plate 14. To do so, the fixation element 22 is advanced through the aperture 300 of the first jaw 304 and into the aperture 80 of the bone plate. The threads 318 of the fixation element 22 engage the threads 88 defined by the aperture 80 to thereby securely or otherwise fixedly couple the plate 14 to the first jaw 204. At this point, the forceps 18 are fixedly coupled to the bone plate 14 such that the bone plate 14 cannot move relative to the forceps 18.

As shown in FIGS. 5B and 5C, a bone anchor 38a may then be inserted through the access aperture 304 of the first jaw 204 and into the bone anchor aperture 76 of the bone plate 14 to thereby affix the first body portion 64 of the bone plate 14 to the first bone segment 30a. Prior to the bone anchor 38a being inserted, a drill bit may be inserted through the access aperture 304 and the bone anchor aperture 76 to form a hole in the bone segment 30a that will be configured to receive the bone anchor 38a. When the first jaw 204 is fixedly coupled to the bone plate 14 and the bone plate 14 is affixed to the first bone segment 30a, it can be said that the first jaw 204 is operatively coupled to the first bone segment 30a.

As shown in FIG. 5D, the second jaw 212 may then be positioned such that the aperture 326 is positioned over the slot 114 of the bone plate 14. In particular, the aperture 326 of the second jaw 212 may be positioned proximate to a distal side of the slot 114. Once positioned, the K-wire 26 may be advanced through the aperture 326 and into the slot 114 such that the distal end 330 of the K-wire 22 engages or otherwise extends into the second bone segment 30b, as shown in FIG. 5E. At this point it can be said that the second jaw 212 is operatively coupled to the second bone segment 30b.

Next, the forceps 18 are actuated so as to drive the first and second jaws 204 and 212 together such that at least one of the engagement members 224 of the first and second jaws 204 and 212 moves along the longitudinal direction. As the engagement members 224 move together, at least one of the first and second bone segments 30a and 30b will be moved toward the other such that the bone gap 34 is reduced. In this way the relative positions of the first and second bone segments 30a and 30b are adjusted in relation to each other. Once the bone segments have been compressed and the bone gap 34 reduced, a second bone anchor 38b may be advanced through the aperture 106 of the second body portion 68 of the bone plate 14 so as to affix the second body portion 68 to the second bone segment 30b, as shown in FIG. 5G. Finally, the forceps 18 and K-wire 26 may be removed, leaving the bone plate 14 affixed to the compressed bone segments 30a and 30b as shown in FIG. 5H.

In another embodiment and in reference to FIG. 6, the bone fixation system may include a forceps having levers that are pivotally connected at a joint similar to the forceps shown in FIGS. 4A-4F, except the forceps shown in FIG. 6 includes jaws that are configured in accordance with another embodiment. As shown in FIG. 6, the levers may include first and second jaws 400 and 404 respectively that are configured to compress the first and second bone segments 30a and 30b together so as to reduce the bone gap 34. As shown, the first and second jaws 400 and 404 each include an engagement member 408 disposed at a distal end of a respective extension 414.

As shown in FIG. 6, each extension 414 is substantially parallel to the outer surface of the bone plate and is configured such that when the forceps are compressed, the extensions 414 are capable of bringing the engagement members 408 together. In that regard, the extension 414 of the second jaw 404 is positioned vertically higher in the transverse direction than the extension 414 of the first jaw 400. Therefore, when the jaws 400 and 404 are compressed together, the extension 414 of the second jaw 404 will at least partially overlap with the extension 414 of the first jaw 400. This allows the engagement members 408 of the first and second jaws 400 and 404 to abut up against each other when the first and second jaws 400 and 404 are fully compressed without interference from the other.

As shown in FIG. 6, the engagement member 408 of the first jaw 400 may be configured to be fixedly coupled to the bone fixation plate, such as bone fixation plate 420 shown in FIGS. 7A and 7B. As shown, the first jaw 400 includes a first or fixation element receiving aperture 424 that extends transversely through the engagement member 408, such that the central axis of the aperture 424 will be generally perpendicular to the outer surface of the bone plate 420. The aperture 424 is configured to receive a fixation element 430 such that the fixation element 430 extends completely through the aperture 424 and engages the bone plate 14 so as to fixedly couple the first jaw 400 to the bone plate 420.

As shown, the fixation element 430 is a guide tube 434 having a tube body 438, and a bore 442 that extends transversely through the tube body 438 and thus includes a central axis that is substantially perpendicular to the outer surface of the bone plate 420. The guide tube 434 may also include a coupler 446 that extends from a distal end of the tube body 438. In the illustrated embodiment, the coupler 446 defines external threads 450 that are configured to engage internal threads defined by an aperture of the bone fixation plate 420. The guide tube 434 may be fixedly coupled to the first jaw 400 with either a nut, an interference fit or any other structure capable of fixedly coupling the guide tube 434 to the first jaw 400. For example, in the illustrated embodiment, the guide tube body 438 defines a recess that is configured to be engaged by a rib or other structure within the bore 442. When the guide tube 434 is fixedly coupled to the bone fixation plate 420 and the tube body 438 is inserted into the aperture 424 of the first jaw 400 such that the rib engages the recess of the tube body 438, the first jaw 400 will be fixedly coupled to the bone fixation plate 420. It should be understood that the guide tube 434 may also be integrally formed with the first jaw 400, and the bone plate 420 may be fixedly coupled to the first jaw 400 prior to the bone plate 420 being positioned against the bone 30.

As shown in FIG. 6, the bore 442 of the guide tube 434 is configured to receive a temporary fixation element 452, which is illustrated as a K-wire 454 having a distal end 458 that is configured to engage or otherwise extend into the first bone segment 30a so as to operatively couple the first jaw 400 to the first bone segment 30a. Therefore, like the bore 442, the K-wire 454 will have a central axis that extends substantially perpendicular to the outer surface of the fixation plate 420.

As shown in FIG. 6, the second jaw 404 includes a temporary fixation element receiving aperture 460 that extends transversely through the engagement member 408 of the second jaw 404 such that a central axis of the aperture 460 is generally perpendicular to the outer surface of the bone fixation plate 420. The aperture 460 is sized to receive or otherwise mate with a guide tube 464 having a guide tube body 468 and a bore 472 extending transversely through the body 468. The bore 472 is sized to receive a temporary fixation element 476, which is illustrated as a K-wire 480 having a distal end 484 that is configured to engage the second bone segment 30b. Therefore the K-wire 480 may extend through the bore 472 through the bone plate 420 and into the second bone segment 30b. It should be understood, however, that the temporary fixation element 476 may be inserted through the aperture 460 without the use of the guide tube 464.

As shown in FIGS. 7A and 7B, the bone fixation plate 420 may be configured to affix the first and second bone segments 30a and 30b to each other. The bone fixation plate 420 can be made in different shapes and sizes for use in a wide variety of clinical applications. The bone fixation plate 420 includes a bone plate body 500 that extends substantially along a central longitudinal axis 504, and defines a proximal end 508 and a distal end 512 opposite the proximal end 508 along the longitudinal axis 504. The plate body 500 further defines a bone facing inner surface 516 and an opposed outer surface 520 spaced from the inner surface 516 along the transverse direction T. The plate body 500 further defines opposed side surfaces 524 and 528 that are spaced from each other along the lateral direction A.

As shown in FIGS. 7A and 7B, the plate body 500 includes a first body portion 534 and an adjoining second body portion 538. The first and second body portions 534 and 538 may be integrally formed (i.e. one single member) and may be configured to contour to the underlying bone 30. In particular, the bone fixation plate 420 is configured to span the bone gap 34 such that the first body portion 534 at least partially contours to the first bone segment 30a and the second body portion 538 at least partially contours to the second bone segment 30b.

With continuing reference to FIGS. 7A-7B, the bone plate 420 defines a plurality of apertures 572 that extend transversely through the plate body 500, from the bone-facing inner surface 516 through to the outer surface 520. In particular, the first body portion 534 of the plate body 500 defines at least two apertures 572, and the second body portion 538 of the plate body 500 defines at least two apertures 572, though it should be understood that any number of apertures 572 may extend through the first and second body portions 534 and 538. As shown the apertures 572 may be aligned along a longitudinal direction or central axis of the bone plate 420.

As shown, the first body portion 534 of the bone fixation plate 420 includes a first or bone anchor aperture 576 that is configured to receive a bone anchor 38, and a second or fixation element receiving aperture 580 that is configured to receive the fixation element 430. The first aperture 576 extends through the bone fixation plate 420 and is configured to receive the bone anchor 38a so as to affix the first body portion 534 of the bone fixation plate 420 to the first bone segment 30a. The first aperture 576 may be a variable angle hole defined by an interior surface 577 that includes a plurality of vertical or transversely extending columns 578. In accordance with the illustrated embodiment, four columns 578 are equidistantly spaced circumferentially about the hole, though the hole may include any number of columns 578 as desired. Each column 578 presents internal threads 579 such that, if the columns 578 were expanded to join each other (i.e. if extended completely around the interior surface 577), the columns 578 would form a continuous helical thread that extends about the central transverse axis of the hole. Thus, it can be said that the threads 579 of adjacent columns 578 are operatively aligned with each other. The columns 578 are circumferentially spaced from each other so as to define corresponding axes that are angled with respect to the transverse central axis, such that a screw can extend through the hole 576, an any of the angled axes while threadedly fixed to the threads 579.

The interior surface 577 that defines the hole further includes a plurality of arcuate pockets 581 that project into the plate body at a location circumferentially between the adjacent columns 578. The pockets 581 each presents an arcuate surface 582 that is concave with respect to a direction radially outward from the central axis of the hole. The bone anchor 38 can be provided as a variable locking bone anchor that can threadedly engage the threads 579 at variable angular positions. Alternatively, the bone anchor 38 can be provided as a fixed angle locking screw. The variable angle hole can be configured to allow the bone anchor to engage the threads 579 at any angular orientation as desired, up to +/−15° (e.g., within a 30° range) with respect to the central axis, which extends along the transverse direction T.

As shown in FIGS. 7A and 7B, the second aperture 580 also extends through the bone fixation plate 420 and includes a coupler 584 that is configured to be engaged by the fixation element 430 so as to fixedly couple the first jaw 400 to the bone fixation plate 420. In the illustrated embodiment, the coupler 584 includes internal threads 588 that are configured to be engaged by the external threads 450 defined by the fixation element 430. It should be understood, however, that the coupler 584 may include structure other than the internal threads 588. For example, the coupler 584 may define a snap on mounting.

As shown, the second body portion 538 of the bone fixation plate 14 includes a first or bone anchor aperture 606 that is configured to receive a bone anchor 38, and a second aperture 610 that is configured to receive the K-wire 454. The first aperture 606 extends through the bone fixation plate 420 and is configured to receive the bone anchor 38b so as to affix the second body portion 538 of the bone fixation plate 420 to the second bone segment 30b. The first aperture 606 is identical to the first aperture 576 of the first body portion 534 of the bone plate 420, and therefore includes the columns 578 and the pockets 581 as described above.

As shown in FIGS. 7A and 7B, the second aperture 610 also extends through the bone fixation plate 420 and defines a K-wire slot 614 that is configured to receive the K-wire 454 such that the K-wire 454 can engage the second bone segment 30b. As shown in FIG. 7B, the K-wire slot 614 has a lateral width Ws and a longitudinal length Ls that is substantially greater than the lateral width Ws. The lateral width Ws of the K-wire slot 614 may be substantially equal to the diameter of the K-wire 454 so as to prevent lateral misalignment of the bone fixation plate 420 during the compression of the bone segments, while at the same time allowing the K-wire 454 to translate within the slot 614 along the longitudinal direction L. The longitudinal length Ls of the K-wire slot 614 may be a length that allows the K-wire 454 and thus the second bone segment 30b to translate toward the first bone segment 30a upon compression of the forceps. It should be understood, however, that the second aperture 610 may have any dimension desired. For example, the second aperture 610 may be a K-wire slot having a lateral width that is greater than the diameter of the K-wire or the second aperture 610 may define a shape other than a slot that allows the K-wire to translate.

In operation and in reference to FIGS. 8A-8E, the bone plate 420 is aligned with and placed over or on the underlying bone 30 such that the bone anchor aperture 576 of the first body portion 534 of the plate 420 is aligned with the first bone segment 30a, and the bone anchor aperture 606 of the second body portion 538 of the plate 420 is aligned with the second bone segment 30b. Either prior to or after the bone fixation plate 420 has been aligned with the bone 30, the forceps 18 may be fixedly coupled to the bone plate 420. To do so, the fixation element 430 is advanced through the aperture 424 of the first jaw 400 and into the aperture 580 of the bone plate 420. The threads 450 of the fixation element 430 engage the threads 588 defined by the aperture 580 to thereby securely couple the plate 420 to the first jaw 400. At this point, the forceps are fixedly coupled to the bone plate 420 such that the bone plate 420 cannot move relative to the forcep.

Figure 8C:
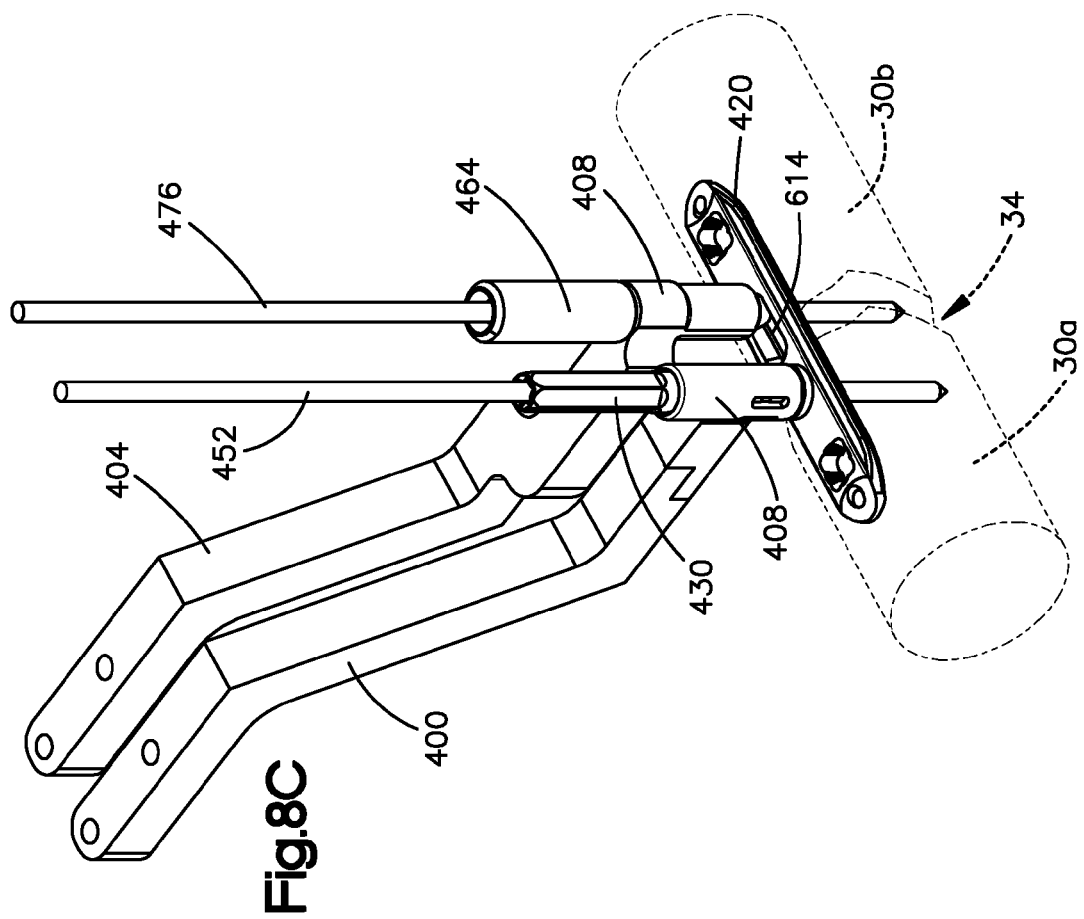
FIG. 8C is a perspective view of the second temporary fixation element extending through both the second jaw, and the slot, and then into the second bone segment so as to couple the second jaw to the second bone segment.

As shown in FIGS. 8B and 8C, the temporary fixation element 452 may be inserted through the bore 442 of the fixation element 430 and into the first bone segment 30a and the second temporary fixation element 476 may be inserted through the aperture 460 either directly or via the bore 472 of the guide tube 464 and into the second bone segment 30b. At this point the first and second jaws 400 and 404 are operatively coupled to the first and second bone segments 30a and 30b.

In reference to FIG. 8D, the forceps 18 may then be actuated so as to drive the first and second jaws 400 and 404 together such that at least one of the engagement members 408 of the first and second jaws 400 and 404 moves along the longitudinal direction. As the engagement members 408 move together, at least one of the first and second bone segments 30a and 30b will be moved toward the other such that the bone gap 34 is reduced. In this way, the relative positions of the first and second bone segments 30a and 30b are adjusted in relation to each other. Once the bone segments have been compressed and the bone gap 34 reduced, the first and second bone anchors 38a and 38b may be advanced through the apertures 576 and 606 of the bone plate 420 so as to affix the bone plate 420 to the first and second bone segments 30a and 30b, as shown in FIG. 5E. Finally, the forceps 18 and K-wires 452 and 476 may be removed, leaving the bone plate 420 affixed to the compressed bone segments 30a and 30b.

It should be appreciated that the bone fixation system can be provided as a kit with one or more, up to all, of the components disclosed, including but not limited to one or more bone fixation plates that can be sized and shaped the same or differently, a plurality of temporary fixation elements that can be sized and shaped the same or differently, a plurality of bone anchors configured the same or differently, and one or more forceps configured the same or differently. It should be appreciated that the components of the bone kit can be provided as described above with respect to the various embodiments and alternative embodiments. Furthermore, the components of the kit can be sold contemporaneously in a common packaging, or at different times in different packaging.

It should be appreciated that the methods described herein can include the step of coupling the first jaw of the forceps to the bone plate without first placing the bone fixation plate over the bone segments, such that the forceps will be fixedly coupled to the plate and can be used to position the bone plate.

The embodiments described in connection with the illustrated embodiments have been presented by way of illustration, and the present invention is therefore not intended to be limited to the disclosed embodiments. Furthermore, the structure and features of each of the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

What is claimed:

1. A method of fixing a bone plate having a first body portion and a second body portion to first and second bone segments that are disposed in a relative position in relation to each other and are separated by a bone gap, the method comprising:
    aligning the bone plate with the first and second bone segments such that a first plurality of apertures extending through the first body portion of the bone plate are generally aligned with the first bone segment and a second plurality of apertures extending through the second body portion of the bone plate are generally aligned with the second bone segment;
    coupling a forceps having first and second jaws to the bone plate by inserting a fixation element through the first jaw and into a first aperture of the first plurality of apertures;
    affixing the first body portion of the bone plate to the first bone segment;
    coupling a temporary fixation element to the second bone segment, the temporary fixation element extending through the second jaw of the forceps and through a first aperture of the second plurality of apertures, the first aperture of the second plurality of apertures defining an elongated slot; and
    actuating the forceps to bias at least the temporary fixation element to translate relative to the bone plate, thereby adjusting the relative positions of the first and second bone segments closer to each other.

2. The method of claim 1, wherein the bone plate is coupled to the forceps prior to aligning the bone plate with the first and second bone segments.

3. The method of claim 1, further comprising affixing the second body portion of the bone plate to the second bone segment.

4. The method of claim 3, wherein the first and second body portions of the bone plate are affixed to the first and second bone segments with bone anchors.

5. The method of claim 1, further comprising compressing the first and second jaws toward each other so as to apply a biasing force to at least one or both of the corresponding fixation element and temporary fixation element.

6. The method of claim 1, wherein the first body portion includes a second aperture of the first plurality of apertures that is configured to be engaged by a positioning element defined by the forceps, the method further comprising aligning the forceps and the bone plate with a defined position.

7. The method of claim 6, further comprising preventing rotation of the bone plate relative to the forceps.

8. The method of claim 1, further comprising preventing lateral misalignment of the bone plate during adjustment of the relative positions of the first and second bone segments in relation to each other.

9. The method of claim 8, further comprising, while preventing lateral misalignment, simultaneously allowing the temporary fixation element to translate within the first aperture of the second plurality of apertures along a longitudinal direction.

10. The method of claim 1, further comprising removing the temporary fixation element from the second bone segment.

11. A method of fixing a bone plate having a first body portion and a second body portion to first and second bone segments that are disposed in a relative position in relation to each other and are separated by a bone gap, the method comprising:
    aligning the bone plate with the first and second bone segments such that a first plurality of apertures extending through the first body portion of the bone plate are generally aligned with the first bone segment and a second plurality of apertures extending through the second body portion of the bone plate are generally aligned with the second bone segment;
    after the aligning step, inserting a bone anchor through a first aperture of the first plurality of apertures and into the first bone segment to couple the bone plate to the first bone segment;
    coupling a forceps having first and second jaws to the bone plate by inserting a fixation element through the first jaw and into a second aperture of the first plurality of apertures, the forceps including a first lever and an opposed second lever that are pivotally connected, the first lever defining a first handle and the second lever defining a second handle;
    coupling a temporary fixation element to the second bone segment, the temporary fixation element extending through the second jaw of the forceps and through an elongated, slotted aperture of the second plurality of apertures; and
    actuating the forceps to cause the first and second jaws to move closer together and bias at least the temporary fixation element to translate relative to the bone plate, thereby adjusting the relative positions of the first and second bone segments in relation to each other.

12. The method of claim 11, wherein at least a portion of the first aperture of the first plurality of apertures is tapered.

13. The method of claim 11, wherein the second aperture of the first plurality of apertures is a threaded hole, and a distal portion of the fixation element is a threaded shaft.

14. The method of claim 11, wherein the elongated, slotted aperture of the second plurality of apertures has a lateral width that is substantially equal to a diameter of the temporary fixation element.

* * * * *